US006261834B1

(12) United States Patent
Srivastava

(10) Patent No.: US 6,261,834 B1
(45) Date of Patent: *Jul. 17, 2001

(54) VECTOR FOR GENE THERAPY

(75) Inventor: Arun Srivastava, Indianapolis, IN (US)

(73) Assignee: Research Corporation Technologies, Inc., Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 07/982,193

(22) Filed: Nov. 25, 1992

Related U.S. Application Data

(63) Continuation-in-part of application No. 07/789,917, filed on Nov. 8, 1991, now Pat. No. 5,252,479.

(30) Foreign Application Priority Data

Nov. 6, 1992 (WO) .................................. PCT/US92/09769

(51) Int. Cl.$^7$ ............................. C12N 15/861; C12N 5/16
(52) U.S. Cl. ...................... 435/320.1; 435/325; 435/372
(58) Field of Search ............................. 435/235.1, 240.2, 435/320.1, 325, 372, 375, 456, 462; 536/23.1, 24.1, 24.5

(56) References Cited

U.S. PATENT DOCUMENTS

| 5,139,941 | 8/1992 | Muzyczka et al. . |
| 5,173,414 | 12/1992 | Lebkowski et al. . |
| 5,252,479 | * 10/1993 | Srivastava .......................... 435/235.1 |

FOREIGN PATENT DOCUMENTS

WO88/08450  11/1988  (WO) .

OTHER PUBLICATIONS

Izban et al. (1989), J. Biol. Chem. 264 (16): 9171–9179.*
Kim et al. (1985), Cell 42: 129–138.*
Lu et al. (1987), J. Immunol. 139(6): 1823–1829.*
Ohi et al. (1990) "Construction and Replication of an Adeno–Associated Virus Expression Vector that Contains Humanβ—Globin", *Gene 89*, 279–282.
Vincent et al. (1990) "Replication and Packaging of HIV Envelope Genes in a Novel Adeno–Associated Virus Vector System", *Vaccines* Cold Spring Harbor Laboratory, New York, 353–359.
Blundell *et al.* (1987) "In Vitro Identification of a B19 Parvovirus Promoter", *Virology 157*, 534–538.
Blundell et al . (1989) "A GC–Box Motif Upstream of the B19 Parvovirus Unique Promoter is Important for In Vitro Transcription", *J. Virol. 63*, 4814–4823.
Doerig et al. (1987) "A Transcriptional Promoter of the Human Parvovirus B19 Active In Vitro and In Vivo", *Virology 157*, 539–542.
Doerig et al. (1990) "Nonstructural Protein of Parvoviruses B19 and Minute Virus of Mice Controls Transcription", *J. Virol. 64*, 387–395.

Hermonat et al. (1984) "Use of Adeno–Associated Virus as a Mammalian DNA Cloning Vector:Transduction of Neomycin Resistance into Mammalian Tissue Culture Cells", *Proc. Natl. Acad. Sci. USA 81*, 6466–6470.
Kotin et al. (1990) "Site–Specific Integration by Adeno–Associated Virus", *Proc. Natl. Acad. Sci. USA 87*, 2211–2215.
Lebkowski et al. (1988) "Adeno–Associated Virus:A Vector System for Efficient Introduction and Integration of DNA into a Variety of Mammalian Cell Types", *Mol. Cell. Biol. 8*, 3988–3996.
Samulski et al. (1982) "Cloning of Adeno–Associated Virus into pBR322:Rescue of Intact Virus from the Recombinant Plasmid in Human Cells", *Proc. Natl. Acad. Sci. USA 79*, 2077–2081.
Samulski et al. (1989) "Helper–Free Stocks of Recombinant Adeno–Associated Viruses:Normal Integration does not Require Viral Gene Expression", *J. Virol. 63*, 3822–3828.
Shade et al. (1986) "Nucleotide Sequence and Genome Organization of Human Parvovirus B19 Isolated from the Serum of a Child During Aplastic Crisis", *J. Virol. 58*, 921–936.
Srivastava et al. (1983) "Nucleotide Sequence and Organization of the Adeno–Associated Virus 2 Genome", *J. Virol. 45*, 555–564.
Srivastava et al. (1989) "Construction of a Recombinant Human Parvovirus B19: Adeno–Associated Virus 2 (AAV) DNA Inverted Terminal Repeats are Functional in an AAV–B19 Hybrid Virus", *Proc. Natl. Acad. Sci. USA 86*, 8078–8082.
McLaughlin et al. (1988) "Adeno–Associated Virus General Transduction Vector: Analysis of Proviral Structures", *Journal of Virology 62*, 1963–1973.
Tratschin et al. (1984) "A Human Parvovirus, Adeno–Associated Virus, as a Eucaryotic Vector:Transient Expression and Encapsidation of the Procaryotic Gene for Chloramphenicol Acetyltransferase", *Mol. and Cell. Biol. 4*, 2072–2081.

* cited by examiner

*Primary Examiner*—John L. LeGuyader
*Assistant Examiner*—Thomas Larson
(74) *Attorney, Agent, or Firm*—Scully, Scott, Murphy & Presser

(57) ABSTRACT

Gene therapy involves the transfer and stable insertion of new genetic information into cells. The present invention is directed to safe vectors for gene therapy and thus provides hybrid parvovirus vectors which are capable of site-specific integration into a mammalian chromosome without substantial cytotoxicity, and which direct erythroid cell-specific expression of heterologous genes. The hybrid vector is useful in gene therapy, particularly in the treatment of hemoglobinopathies and other hematopoietic diseases, and in conferring cell-specific multidrug resistance. A method of delivery of constitutive levels of a pharmaceutical product and a method of producing a recombinant protein are also provided.

15 Claims, 20 Drawing Sheets

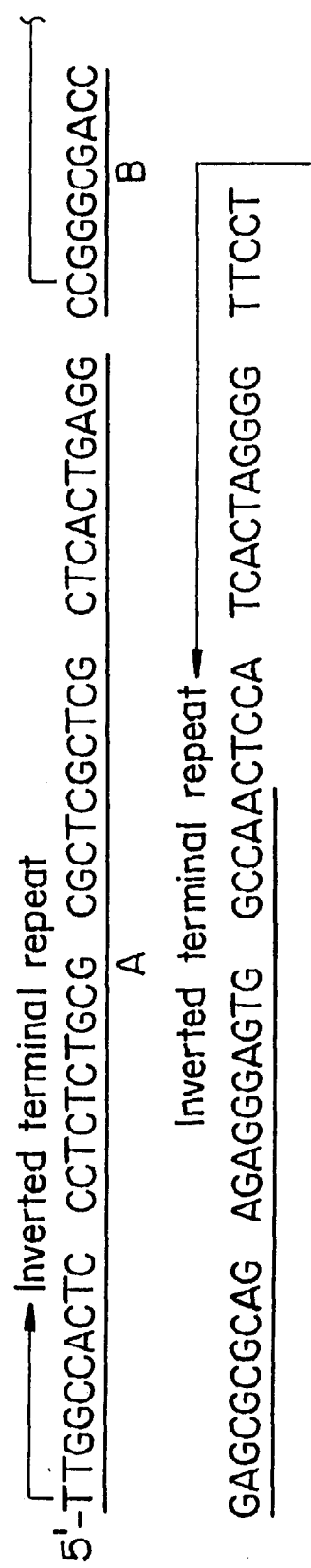
FIG. IA

```
ATTTTAAGTGTGTTTACTATATAATTTTATTGGTTAGTTTTTGTAACGGTTAAAATGGGCGGAGCGTAGGCGGGA
TAAAATTCACAAAATGATATATTAAAATCAAAACATTGCCAATTTTACCCGCCTCGCATCCGCCCCT
                       EcoRI*                        MaeIII
                                 260                    280              300

GCTTTTTCCTGGACTTTCTTGCTGTTTTTGTGAGCTAACAGGTATTTATACTACTTGTT
CGAAAAAGGACCTGAAAGAACGACAAAAAACACTCGATTGTCCATAAATATGATGAACAA
     BstNI                          AluI                    Hpa
     ScrFI                                                   Hin
              380              400                    420
```

FIG. 2A

```
                     220                                  240
TTTTAGCGGGGCTTTTTCCCGCCTTATGCAAAATGGGCAGCC
AAAATCGCCCCGAAAAAGGGCGGAATACGTTTTACCCGTCGG
                                              BbvI 320                340                      360
CTACAGTATATATAGCACACGGTACTGCCGCAGCTCTTTCTTTCTGGCT
GATGTCATATATATCGTGTGCCATGACGGCGTCGAGAAAGAAAGACCCGA
                        RsaI     BbvI              BbvI
```

FIG. 2B

AAV-mediated transfer of Neo$^r$ to human hematopoietic stem cells.

A. Neo gene expression under the control of the the TK promoter

AAV-medicated transfer of Neo to human hematopoietic stem cells.

B. Neo gene expression under the control of the B19p6 promotor

SEQUENCE LISTING (1) GENERAL INFORMATION:

(iii) NUMBER OF SEQUENCES: 2

(2) INFORMATION FOR SEQ ID NO: 1:

```
          (i) SEQUENCE CHARACTERISTICS:
              (A) LENGTH: 145 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 1:

TTGGCCACTC CCTCTCTGCG CGCTCGCTCG CTCACTGAGG CCGGGCGACC AAAGGTCGCC        60

CGACGCCCGG GCTTTGCCCG GGCGGCCTCA GTGAGCGAGC GAGCGCGCAG AGAGGGAGTG       120

GCCAACTCCA TCACTAGGGG TTCCT                                            145

(2) INFORMATION FOR SEQ ID NO: 2:

(i) SEQUENCE CHARACTERISTICS:
              (A) LENGTH: 225 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 2:

TTTTAGCGGG CTTTTTTCCC GCCTTATGCA AATGGGCAGC CATTTTAAGT GTTTTACTAT        60

AATTTTATTG GTTAGTTTTG TAACGGTTAA AATGGGCGGA GCGTAGGCGG GGACTACAGT       120

ATATATAGCA CGGTACTGCC GCAGCTCTTT CTTTCTGGGC TGCTTTTTCC TGGACTTTCT       180

TGCTGTTTTT TGTGAGCTAA CTAACAGGTA TTTATACTAC TTGTT                      225
```

VECTOR FOR GENE THERAPY

This application is a continuation-in-part of application U.S. Ser. No. 789,917 filed Nov. 8, 1991 now U.S. Pat. No. 5,252,479.

This invention was made with Government support under A1-26323 awarded by NIH. The Government has certain rights in the invention.

FIELD OF THE INVENTION

Gene therapy involves the transfer and stable insertion of new genetic information into cells. The present invention is directed to a safe vector for gene therapy and provides hybrid parvovirus vectors which are capable of site-specific integration into a mammalian chromosome without substantial cytotoxicity, and which can direct cell-specific expression of a desired gene product. The hybrid vectors are useful in gene therapy, particularly in the treatment of hemoglobinopathies. A method of delivery of a pharmaceutical product is also provided. The present invention also provides a method of conferring cell-specific multidrug resistance.

BACKGROUND OF THE INVENTION

The therapeutic treatment of diseases and disorders by gene therapy involves the transfer and stable insertion of new genetic information into cells. The correction of a genetic defect by re-introduction of the normal allele of a gene encoding the desired function has demonstrated that this concept is clinically feasible [Rosenberg et al. (1990) *New Eng. J. Med.,* 323, 570].

Hematopoietic stem cells or pluripotent progenitor cells are particularly useful for gene therapy studies since, although they are somatic cells, they differentiate to produce all the lineages of blood cells. Hence, the introduction of a foreign gene into a stem or progenitor cell results in the production of various lineages which can potentially express the foreign gene or alter control of native gene products. The introduction of a foreign gene into a progenitor cell or any other appropriate cell requires a method of gene transfer to integrate the foreign gene into the cellular genome. Although a variety of physical and chemical methods have been developed for introducing exogenous DNA into eukaryotic cells, viruses have generally been proven to be much more efficient for this purpose. Several DNA-containing viruses such as parvoviruses, adenoviruses, herpesviruses and poxviruses, and RNA-containing viruses, such as retroviruses, have been used to develop eukaryotic cloning and expression vectors. The fundamental problem with retroviruses is that they are either the etiologic agents of, or are intimately associated with, malignancy. Retroviruses integrate randomly into the cellular genome, and thus may activate cellular proto-oncogenes or may disrupt sequences critical to cell function. Accordingly, the use of retroviral vectors in gene transfer presents a problem in that there is a finite chance that such vectors may induce neoplasia. Thus, a need exists for additional and improved vectors for gene transfer.

Whereas retroviruses are frequently the etiologic agents of malignant disorders, parvoviruses constitute the sole group of DNA-containing viruses that have not yet been associated with any malignant disease. Although parvoviruses are frequently pathogenic in animals, a parvovirus of human origin, the adeno-associated virus 2 (AAV), has so far not been associated with any known human disease, even though up to 90% of the human population has been exposed to AAV. [Blacklow, N. R. (1988) in: *Parvoviruses and Human Disease*, CRC Press, Boca Raton]. In addition, most retroviruses used for gene transfer are of murine origin, while AAV, a human virus, is physiologically more relevant for gene transfer in humans. Moreover, retroviruses are susceptible to inactivation by heat and organic solvents, whereas AAV is heat stable, extremely resistant to lipid solvents, and stable between pH 3.0 and 9.0. Thus as vehicles for gene transfer, parvoviruses provide many advantages over retroviruses.

Recombinant retroviruses have low viral titers ($10^5$–$10^6$ virions/ml) (Rosenberg) in contrast to the high titers of recombinant AAV ($10^8$–$10^9$ virions/ml) [Srivastava et al. (1990) *Blood* 76, 1997]. Consequently, it is generally not possible to achieve an infection efficiency with recombinant retrovirus beyond 10–50% of the target cell population, with successful infection requiring actively replicating cells. In contrast, a 70% infection efficiency has been reported for a recombinant AAV [Samulski et al. (1989) *J. Virol.* 63, 3822], and it is possible to achieve a 100% infectivity of target cells with wild-type AAV [Nahreini et al. (1989) *Intervirol.* 30, 74]. Furthermore, even though recombinant retroviral vectors have been rendered replication-incompetent, there remains a low probability of recombination between the vector and endogenous retroviral sequences. In contrast, 60–90% of the population is sero-positive for human parvoviruses, and no endogenous viral sequences have yet to be detected in volunteer donors. In recombinant AAV vectors, all of the AAV coding sequences have, nonetheless, been deleted.

Perhaps the most significant advantages of AAV-based vectors are that they mediate integration into the host chromosomal DNA in a site-specific and stable manner. Retroviral genomes, following reverse transcription, undergo integration into the host chromosomal DNA with a totally random integration pattern. AAV establishes a latent infection which is site-specific. The integration site has been mapped to human chromosome 19. (Kotin et al. (1990) *Proc. Natl. Acad. Sci. USA* 87, 2211). It has therefore become feasible to accomplish site-specific delivery of exogenous DNA into mammalian cells. While retroviral vectors mediate integration of non-viral sequences into the host chromosome, the integration pattern is not always stable. Frequently the integrated retroviral provirus is excised from the cell. AAV, on the other hand, establishes a stable integration.

Despite the potential advantages outlined above, the parvovirus-based vectors suffer from one limitation, and that is the size of a DNA sequence that can be packaged into the mature virions. For example, whereas up to 8.0–9.0 kilobase pair (kbp) DNA fragments can be packaged into retroviral vectors, a maximum of about 5.0 kbp DNA can be packaged into AAV. This size limitation, however, does not preclude the cloning and packaging of most cDNA molecules.

Thus parvovirus-based vectors offer a useful alternative to retroviral vectors for gene therapy in humans. While AAV-based vectors allow stable, site-specific integration of transferred genes, the indiscriminate expression of the transferred gene in all cell lineages presents significant problems. Thus, a need exists for AAV vectors which effect tissue-specific expression of the transferred gene. In accordance with the present invention, one method, for example, to solve this problem is by a combination of the features of AAV and another human parvovirus, B19.

While AAV causes no known disease, B19 is known to be the etiologic agent of a variety of clinical disorders in humans. B19 is the causative agent of transient aplastic crises associated with various hemolytic anemias, erythema infectiosum or the "fifth disease", post-infection polyarthralgia and thrombocytopenia in adults, and some cases of chronic bone marrow failure and hydrops fetalis.

AAV is dependent on a helper virus, such as adenovirus, herpesvirus, or vaccinia virus, for optimal replication. In the absence of a helper virus, AAV establishes a latent infection in which the viral genome integrates into chromosomal DNA site-specifically. B19, on the other hand, is an autonomously replicating virus that is known to replicate only in human hematopoietic cells in the erythroid lineage. Both AAV and B19 contain linear, single-stranded DNA genomes, but their genomes show no homology at the nucleotide sequence level. The nucleotide sequences of both genomes are known. [Lusby et al. (1980) J. Virol. 34, 402, Srivastava et al. (1983) J. Virol. 45, 555; Shade et al. (1986) J. Virol. 58, 921]. The AAV genome contains inverted terminal repeats (ITRs) of 145 nucleotides, 125 nucleotides of which form a palindromic hairpin that plays a critical role during AAV DNA replication. The sequences of the ITRs are shown in FIG. 1 and as SEQ ID NO:1. In latently infected cells, the termini of AAV are at the junction of the cellular sequences and thus the termini also facilitate integration and rescue.

The remarkable features of the two human parvoviruses can be combined, for example, in an AAV-B19 hybrid vector, to provide vectors in accordance with the present invention. The vectors of this invention are particularly useful for gene transfer in bone marrow cells and other hematopoietic cells. These hybrid viral vectors mediate site-specific integration as well as tissue-specific expression of heterologous genes in hematopoietic cells.

SUMMARY OF THE INVENTION

The present invention is directed to hybrid parvovirus vectors capable of site-specific integration into a mammalian chromosome without substantial cytotoxicity, and which can direct tissue-specific expression of a heterologous gene, i.e. a non-parvovirus gene. More particularly, the present invention provides vectors comprising two inverted terminal repeats of adeno-associated virus 2 and at least one genetic cassette comprising a promoter capable of effecting cell-specific expression operably linked to a heterologous gene wherein the cassette resides between the two inverted terminal repeats. In a preferred embodiment, the promoter is the p6 promoter of B19 parvovirus and directs erythroid cell-specific expression of the heterologous gene.

In another aspect of this invention, host cells transduced by the hybrid vectors of the present invention are provided.

Another aspect of the present invention provides a method of treatment for hematopoietic diseases, in particular hemoglobinopathies, by transducing hematopoietic stem or progenitor cells with a vector of a present invention and introducing the transduced cells into a patient, where the heterologous gene is expressed.

A further aspect of this invention provides a method for delivery of a pharmaceutical product in a mammal by transducing hematopoietic stem or progenitor cells with a hybrid vector of the present invention and introducing the transduced cells into the mammal. The heterologous gene is expressed, and the mature red blood cell provides a vehicle for delivery of the heterologous gene product throughout the bloodstream or to the liver or spleen.

Yet another aspect of the present invention provides a method of conferring cell-specific multidrug resistance by transducing cells with a hybrid vector of the present invention in which the heterologous gene is a multidrug resistance gene, and introducing the transduced cells into a mammal. In a preferred embodiment, the hybrid vector contains the B19p6 promoter, and thus the multidrug resistance phenotype is conferred to erythroid cells.

As used herein, transduction refers to a process by which cells take up foreign DNA and integrate that foreign DNA into their chromosomes. Transduction can be accomplished, for example, by transfection, which refers to various techniques described hereinbelow by which cells take up DNA, or infection, by which viruses are used to transfer DNA into cells.

BRIEF DESCRIPTION OF THE DRAWINGS

FIG. 2 depicts the nucleotide sequence of B19 from nucleotide number 200 to nucleotide number 424 as numbered by Shade et al. (1986).

DETAILED DESCRIPTION OF THE INVENTION

Figure 1B:
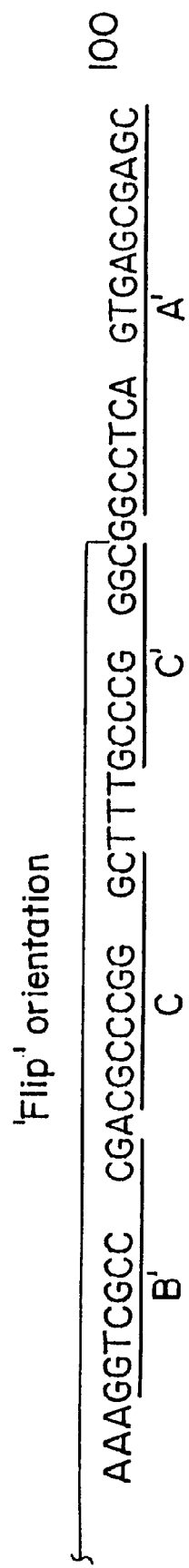
FIG. 1 depicts the nucleotide sequence of an ITR of the AAV 2 genome.

The present invention relates to hybrid parvovirus vectors which comprise a pair of AAV inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus. In accordance with the present invention, AAV and B19 coding regions have been deleted, resulting in a safe, noncytotoxic vector. Representative heterologous genes are described hereinbelow. The AAV ITRs, or modifications thereof, confer infectivity and site-specific integration, but not cytotoxicity, and the promoter directs cell-specific expression and preferably erythroid cell expression using the p6 promoter of B19 parvovirus. The hybrid vectors of the present invention thus provide DNA molecules which are capable of integration into a mammalian chromosome without substantial toxicity. These hybrid vectors allow safe integration of the DNA into the cellular genome, since the portions of the DNA responsible for replication of the parvovirus have been deleted, and therefore these vectors cannot self replicate.

In accordance with the present invention, the hybrid vector comprises a first and second terminal repeat which flank a promoter linked-to a heterologous gene. The terminal repeats can comprise all or part of the ITRs of AAV. The terminal repeats mediate stable integration of the DNA sequence into a specific site in a particular chromosome, e.g. human chromosome 19. The entire DNA sequence, including the ITRs, the promoter, and the heterologous gene can be integrated into the cellular genome.

The terminal repeats of the hybrid vector of the present invention can be obtained by restriction endonuclease digestion of AAV or a plasmid such as psub201, which contains a modified AAV genome [Samulski et al. (1987) *J. Virol.* 61, 3096], or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e. stable and site-specific integration. The ordinarily skilled artisan can also determine which minor modifications of the sequence can be tolerated while maintaining the ability of the terminal repeats to direct stable, site-specific integration. Site-specific integration can be assessed, for example, by Southern blot analysis. DNA is isolated from cells transduced by the vectors of the present invention, digested with a variety of restriction enzymes, and analyzed on Southern blots with an AAV-specific probe. A single band of hybridization evidences site-specific integration. Other methods known to the skilled artisan, such as polymerase chain reaction (PCR) analysis of chromosomal DNA can be used to assess stable integration.

The vectors of the present invention contain a promoter which directs tissue-specific expression. For example, the wild-type parvovirus B19 has a limited host range and exhibits a remarkable tissue tropism for the erythroid elements of bone marrow. In a preferred embodiment, the hybrid vectors of the present invention utilize a transcriptional promoter of B19 to effect tissue-specific expression of heterologous sequences. In a more preferred embodiment the promoter is the p6 promoter of B19, which is active in erythroid progenitor cells. The nucleotide sequence of B19 from nucleotide number 200 to nucleotide number 424 as numbered by Shade et al. (1986) contains the p6 promoter and is depicted in FIG. 2 and as SEQ ID NO:2.

The consensus promoter-like sequence TATATATA is present at nucleotide 320 in B19 (as numbered by Shade et al.) and thus transcription is likely to originate about 30 nucleotides downstream. It has been discovered in accordance with the present invention that B19 fragments containing these sequences direct expression that is specific for erythroid progenitor cells, and that deletion of B19 coding sequences downstream from the promoter prevents replication of B19. As explained above, one of ordinary skill in the art can determine the minimum sequence and modifications of the p6 promoter which provide cell-specific, non-cytotoxic expression. This can be determined by infecting erythroid and non-erythroid cells with vectors containing the B19p6 promoter and assessing expression of the heterologous gene. The promoter sequence can be derived by restriction endonuclease digestion of B19 or a cloned B19 plasmid such as pYT103 and pYT107 [Cotmore et al. (1984) *Science* 226, 1161] or by any other methods known to the skilled artisan, including but not limited to chemical or enzymatic synthesis based upon the published sequence of B19. Other cell-specific promoters can be obtained by analogous methods, and the specificity of these promoters is determined by assessing expression in the appropriate cell type.

The promoter of the hybrid vector is operably linked to the heterologous gene. Any gene that can be transcribed in such a construction is contemplated by the present invention. In a preferred embodiment, the heterologous gene encodes a biologically functional protein, i.e. a polypeptide or protein which affects the cellular mechanism of a cell in which the biologically functional protein is expressed. For example, the biologically functional protein can be a protein which is essential for normal growth of the cell or for maintaining the health of a mammal. The biologically functional protein can also be a protein which improves the health of a mammal by either supplying a missing protein, by providing increased quantities of a protein which is underproduced in the mammal or by providing a protein which inhibits or counteracts an undesired molecule which may be present in the mammal. The biologically functional protein can also be a protein which is a useful protein for investigative studies for developing new gene therapies or for studying cellular mechanisms.

The biologically functional protein can be a protein which is essential for normal growth or repair of the human body. The biologically functional protein may also be one which is useful in fighting diseases such as cancer, atherosclerosis, sickle-cell anemia and the thalassemias. Examples of such biologically functional proteins are hemoglobin ($\alpha$, $\beta$ or $\gamma$-globin), hematopoietic growth factors such as granulocyte-macrophage colony stimulating factor (GM-CSF), macrophage colony stimulating factor (M-CSF), granulocyte colony stimulating factor (G-CSF) and erythropoietin (EPO). Another example is tumor necrosis factor (TNF), which is a molecule that can be used to treat cancer, and in particular, tumors. The tumor suppressors p53 and retinoblastoma (RB) are also contemplated. Various cytokines such as mast cell growth factor (MGS) and interleukins 1–11 are also proteins which are contemplated by the present invention. The biologically functional protein may also be a selectable marker for antibiotic resistance such as a selectable marker for neomycin resistance in eukaryotes. Other types of selectable markers such as adenine phosphoribosyl transferase (APRT) in APRT-deficient cells, or the firefly luciferase gene are also included. The heterologous genes encoding these proteins can be provided by any of a variety of methods, such as routine cloning procedures (Sambrook et al.), excision from a vector containing the gene of interest, or chemical or enzymatic synthesis based on published sequence information. In many instances the DNA encoding the protein of interest is commercially available.

The biologically functional protein can affect cellular mechanism by providing a new or altered function to a cell. For example, the heterologous gene can be a multidrug resistance gene (mdr) which encodes P-glycoprotein. P-glycoprotein is a cell membrane glycoprotein which affects intracellular drug accumulation and is responsible for the phenomenon of mutidrug resistance.(for review, see Biedler [1992] *Cancer* 70 1799)

In another embodiment the heterologous gene can encode a non-biologically functional protein. For example, a hybrid gene comprising various domains and functions from a variety of sources can be designed and produced by recombinant technology or enzymatic or chemical synthesis.

In another preferred embodiment the heterologous gene is capable of being transcribed into an RNA molecule which is sufficiently complementary to hybridize to an mRNA or DNA of interest. Such an RNA molecule is hereinafter referred to as antisense RNA, and has utility in preventing or limiting the expression of overproduced, defective, or otherwise undesirable molecules. The vector of the present invention can comprise, as the heterologous gene, a sequence encoding an antisense RNA which is sufficiently complementary to a target sequence such that it binds to the target sequence. For example, the target sequence can be part of the mRNA encoding a polypeptide such that it binds to and prevents translation of mRNA encoding the polypeptide. In another embodiment, the target sequence is a segment of a gene that is essential for transcription such that the antisense RNA binds the segment (e.g. a promoter or coding region) and prevents or limits transcription. Hence, the antisense RNA must be of sufficient length and complementarity to prevent translation of its target mRNA or transcription of its target DNA.

In a preferred embodiment the antisense RNA is a 15 mer and exhibits 100% complementarity to the target sequence. One of ordinary skill in the art can determine longer or shorter antisense molecules having sufficient complementarity to a target sequence such that the antisense molecule is capable of binding to the target and thereby inhibiting translation or transcription. The heterologous gene can be provided, for example, by chemical or enzymatic synthesis, or from commercial sources.

It is preferable that the length of the heterologous gene is such that the overall size of the hybrid vector is about 5 kilobases (kb), since the packaging limit of AAV virions is about 5 kb (Hermonat et al. (1984) *Proc. Natl. Acad. Sci. USA* 81, 6466).

The hybrid vectors of the present invention can be provided by inserting the heterologous gene and the cell-specific promoter between a pair of AAV-derived terminal repeats. The combination of a promoter and heterologous gene is also referred to herein as a cassette. Thus, the invention provides a vector in which: 1) the terminal repeats mediate stable, site-specific integration into the cellular genome; and 2) the promoter mediates cell-specific expression of a heterologous gene, e.g. in erythroid cells, or the promoter mediates transcription of an antisense RNA or a sense RNA encoding a polypeptide of interest. The promoter sequence is operably linked to the heterologous gene in a manner to effect expression of the gene. Hence, the promoter sequence can be at either or both ends of the heterologous sequence or coding region. Furthermore, more than one promoter and heterologous gene can be present in one vector, i.e. there can be two or more cassettes between the ITRs. Accordingly, more than one heterologous gene can be expressed by one vector.

Standard techniques for the construction of such hybrid vectors are well-known to those of ordinary skill in the art and can be found in references such as Sambrook et al. (1989) in *Molecular Cloning: A Laboratory Manual*, Cold Spring Harbor, N.Y., or any of the myriad of laboratory manuals on recombinant DNA technology that are widely available. A variety of strategies are available for ligating fragments of DNA, the choice of which depends on the nature of the termini of the DNA fragments and can be readily determined by the skilled artisan.

It is further contemplated in accordance with the present invention to include in the hybrid vectors other nucleotide sequence elements which facilitate integration of DNA into chromosomes, expression of the DNA, and cloning of the vector. For example, the presence of enhancers upstream of the promoter or terminators downstream of the coding region can facilitate expression. In another example, recent studies have identified a DNaseI-hypersensitive site (HS-2) upstream of the human globin gene cluster that significantly enhances the erythroid-specific expression of the globin genes. [Tuan et al. (1985) *Proc. Natl. Acad. Sci. USA* 82, 6384]. In the hybrid vectors of the present invention, the presence of HS-2 upstream of the B19p6 promoter enhances tissue specific expression.

Figure 3:
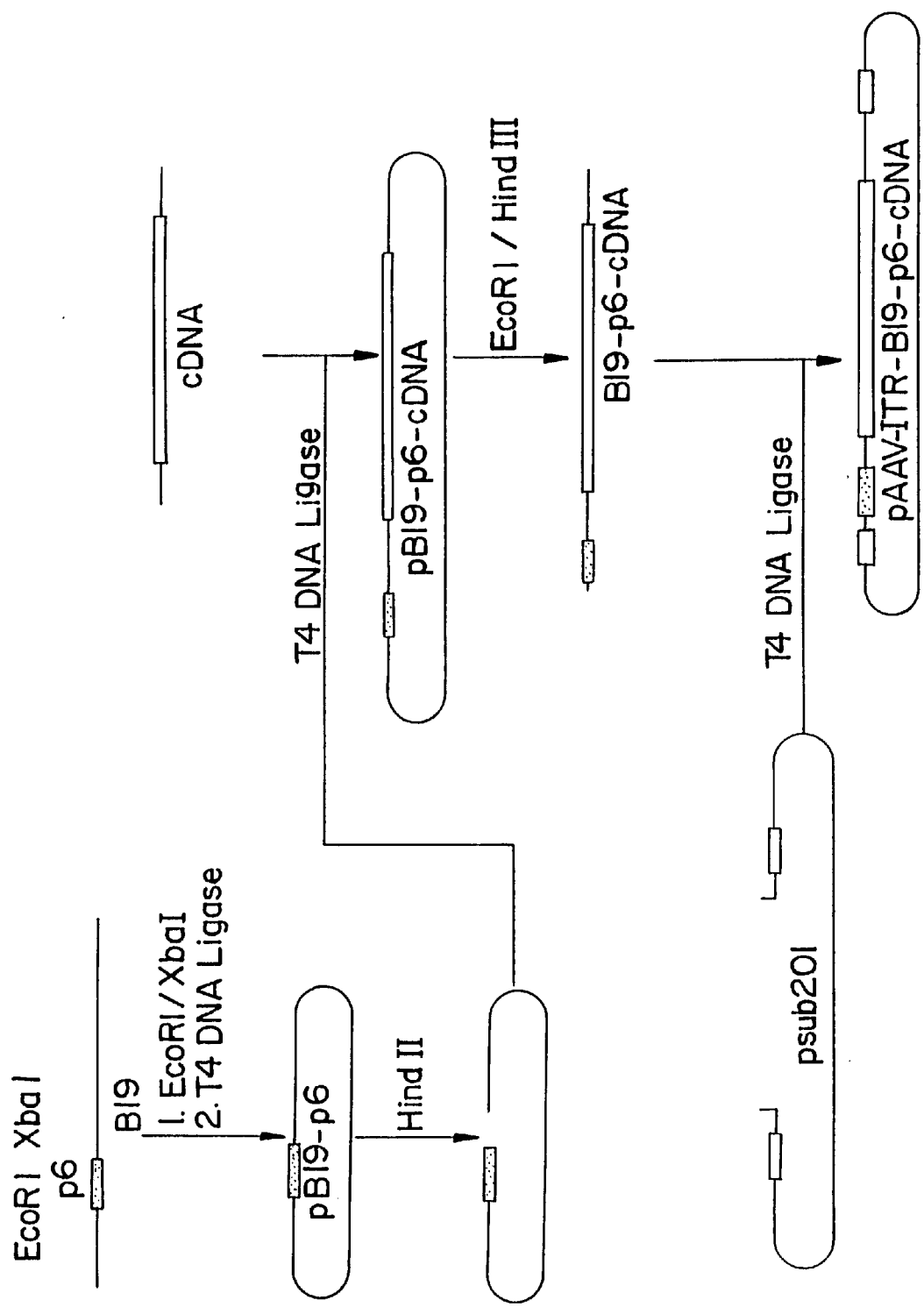
FIG. 3 diagrams the construction of a hybrid vector of the present invention.

As described hereinabove, the vectors of the present invention can be constructed by a variety of well-known methods, and the order of the ligation of the elements can be varied. In a preferred embodiment the cell-specific promoter and heterologous gene are ligated together to provide a cassette which can be inserted between two AAV-ITRS. For example, to provide a cassette containing the B19p6 promoter and a heterologous gene, a fragment containing the p6-promoter is inserted into a pUC19 plasmid, after which the p6 containing plasmid is linearized by restriction enzyme cleavage downstream of the p6 promoter. The heterologous gene is then inserted immediately downstream of the p6 promoter. A fragment containing both the p6 promoter and the heterologous gene is excised from the plasmid and inserted between the AAV-ITRs in an AAV plasmid from which the AAV coding regions have been deleted. The resulting plasmid comprises the p6 promoter and a heterologous gene flanked by a pair of AAV-ITRs. This construction is described more specifically as follows and is diagrammed in FIG. 3. To generate a plasmid containing p6, a fragment containing the p6 promoter of B19 is isolated from B19 DNA or cloned B19 DNA [see, for example, Cotmore et al. (1984); Shade et al. (1986)]. In a preferred embodiment this B19 fragment corresponds to nucleotides 200 to 480 as numbered by Shade et al. (1986) and contains the entire 5' non-coding region and p6 promoter of B19. This 280 bp fragment is flanked by EcoRI and XbaI restriction sites and can be generated by cleavage with these restriction enzymes. This fragment is cloned into the EcoRI-XbaI sites of pUC19 to generate plasmid pB19p6. The skilled artisan will recognize that other plasmids and restriction sites can be utilized to generate a vector comprising a B19p6 promoter. Alternatively, the B19p6 promoter can be synthesized chemically or enzymatically based upon the published sequence and ligated to the heterologous gene.

A heterologous gene can be operably linked downstream of the B19p6 promoter fragment as follows. The plasmid pB19p6 is cleaved with HincII, which cleaves B19 DNA downstream of the p6 promoter (i.e. at nucleotide 424) and also in the multiple cloning site of pUC19. The desired heterologous gene is blunt-end ligated downstream from the B19p6 promoter between the two HincII sites to generate a plasmid pB19p6-insert. The ordinarily skilled artisan will recognize a variety of methods, as exemplified, e.g. in Sambrook et al. (1989), to ligate a fragment containing a cell-specific promoter with a fragment containing the heterologous gene. In accordance with the present invention, the coding sequence of GM-CSF, APRT, neo$^r$, the retinoblastoma gene, α-globin, β-globin and γ-globin have been employed as the heterologous gene, resulting in the construction of hybrid vectors, designated AAV-B19-GM-CSF, AAV-B19-APRT, AAV-B19-neo$^r$, AAV-B19-RB, AAV-B19-α-globin, AAV-B19-β-globin and AAV-B-19-globin, respectively. A multidrug resistance gene encoding P-glycoprotein is also specifically contemplated as the heterologous gene. The coding sequences of the respective genes are known [Lee et al. (1985) *Proc. Natl. Acad. Sci. USA* 82, 4360 (GM-CSF); Broderick et al. (1987) *Proc. Natl. Acad. Sci. USA* 84, 3349 (APRT); Tratschin et al. (1985) *Mol. Cell. Biol.* 5, 3251 (Neo$^r$); Huang et al. (1988) *Science* 242, 1563 (RB-1); Liebhaber et al. (1980) *Proc. Natl. Acad. Sci. USA* 77, 7054 (α-globin); Lawn et al. (1980) *Cell* 21, 647 (β-globin); Enver et al. (1989) *Proc. Natl. Acad. Sci. USA* 86, 7033 (γ-globin) Roninson et al. (1986) *Proc. Nat'l Acad. Sci. USA* 83, 4538; Roninson et al. (1991) in *Molecular and Cellular Biology of Multidrug Resistance in Tumor Cells* (ed. Roninson, Plenum Press, NY) 91–106; Schinkel et al. (1991) *Cancer Res.* 51, 2628; Chen et al. (1990) *J. Biol. Chem.* 265, 506; (mdr)] and thus can be easily provided as described hereinabove.

The pB19p6-insert plasmid exemplifies a promoter-heterologous gene cassette which can be isolated by digesting the plasmid, for example, with EcoRI and HindIII or other appropriate restriction enzymes, and then ligated between two AAV-ITRs. The AAV-ITRs are provided by, for example, restriction digestion of AAV DNA or AAV cloned DNA, or chemical or enzymatic synthesis based upon the published sequence of AAV ITRs [Lusby et al. (1980)]. In a preferred embodiment, the AAV ITRs comprise the 145 nucleotides shown in FIG. 1. Fragments which contain the 125 nucleotides which form the palindromic hairpin (nucleotide 1–125 of FIG. 1) or longer fragments which contain the terminal 191 nucleotides of the viral chromosome are also useful. Additional endogenous sequences, for example linkers to facilitate cloning and ligation, can also be used in the constructs. In a preferred embodiment, the AAV ITRs are provided by a plasmid, e.g. psub201 [Samulski et al. (1987)] which is an AAV derivative into which XbaI cleavage sites have been introduced at sequence positions 190 and 4484, and the right-terminal 191 base pairs of the viral genome have been substituted for the normal left-terminal 190 base pair domain. This modification results in the extension of the psub201 terminal repeats to 191 base pairs. The XbaI cleavage sites allow substitution of the AAV coding region with exogenous sequences, i.e. the B19 promoter and heterologous gene, such that the exogenous sequences are flanked by the AAV-ITRs. Derivatives of psub201 engineered to contain other restriction sites, as demonstrated in Examples 2 and 3, are also useful for providing the AAV-ITRs.

To substitute the B19p6-insert, i.e. the cassette, for the AAV coding region, psub201 is digested with XbaI to delete the AAV coding regions. Plasmid vector DNA containing the AAV-ITRs is isolated and ligated to the B19p6-insert construction. Ligation may be facilitated by the addition of adapters to the AAV-ITRs and linkers to the B19-p6-insert.

For example, in another preferred embodiment the vectors of the present invention are constructed by modifying the engineered XbaI sites of psub201 to provide additional restriction sites, deleting the AAV coding regions by digestion with the appropriate restriction enzyme and ligating the B19p6-insert cassette to the plasmid DNA containing the AAV-ITRS. The construction of prototype plasmid vectors containing the AAV-ITRs but not the AAV coding regions, and which further contain cloning sites to facilitate the insertion of promoter-heterologous gene cassettes, are exemplified in Examples 2 and 3.

The resulting plasmid comprises a cell-specific promoter upstream of a heterologous sequence, both of which are flanked by AAV-ITRs. The order of the ligations, the nature of the complementary ends, the use of linkers and adapters, and other details can be varied as necessary by one of ordinary skill in the art to provide the AAV-B19 hybrid vector of the present invention.

To establish integration of the vector DNA into the chromosome of a host cell, host cells are transfected with the vector or infected with mature virions containing the hybrid vectors. Methods of DNA transfection are well-known to one of ordinary skill in the art and include, for example, naked DNA transfection, microinjection and cell fusion. More efficient integration is accomplished by infection with virions containing the hybrid vectors.

Virions can be produced by coinfection with a helper virus such as adenovirus, herpes virus or vaccinia virus. Following coinfection of host cells with the subject vector and a helper virus, virions are isolated and the helper virus is inactivated. The resulting helper free stocks of virions are used to infect host cells. In another embodiment, virions are produced by cotransfecting helper virus-infected cells with the vector of the present invention and a helper plasmid. For example, the hybrid construct of the present invention can be packaged into mature AAV virions by cotransfection of adenovirus-infected cells with the vector of the present invention and a plasmid which provides the parvovirus rep gene and adenovirus termini. An example of such a plasmid is pAAV/Ad, which contains the entire coding sequence of AAV and the adenovirus type 5 terminal sequences in place of the normal AAV termini. [Samulski et al. (1989)]. Following cotransfection, mature virions are isolated by standard methods, e.g. cesium chloride centrifugation and heated at 56° C. for our hour to inactivate any contaminating adenovirus. The resulting mature virions contain the vector of the present invention and are used to infect host cells in the absence of helper virus.

Function of the hybrid vectors of the present invention, i.e. the ability to mediate transfer and expression of the heterologous gene in a specific cell type, can be evaluated by monitoring the expression of the heterologous gene in transduced cells. For example, bone marrow cells are isolated and enriched for hematopoietic stem cells (HSC), e.g. by fluorescence activated cell sorting as described in Srivastava et al. (1988) *J. Virol.* 62, 3059. HSC are capable of self-renewal as well as initiating long-term hematopoiesis and differentiation into multiple hematopoietic lineages in vitro. HSC are transfected with the vector of the present invention or infected with varying concentrations of virions containing a subject hybrid vector and then assessed for the expression of the heterologous gene.

The assay for expression depends upon the nature of the heterologous gene. Expression can be monitored by a variety of methods including immunological, histo-chemical or activity assays. For example, Northern analysis can be used to assess transcription using appropriate DNA or RNA probes. If antibodies to the polypeptide encoded by the heterologous gene are available, Western blot analysis, immunohistochemistry or other immunological techniques can be used to assess the production of the polypeptide. Appropriate biochemical assays can also be used if the heterologous gene is an enzyme. For example, if the heterologous gene encodes antibiotic resistance, a determination of the resistance of infected cells to the antibiotic can be used to evaluate expression of the antibiotic resistance gene.

In addition to assessing that the heterologous gene is expressed in the appropriate cells, the correct promoter specificity of the hybrid vectors can be evaluated by monitoring the expression of the heterologous gene, or lack of expression, in cells in which the promoter is not expected to be active. For example, when cells from a naso-pharyngeal cell line, KB, are transduced with a hybrid vector containing the B19p6 promoter, the heterologous gene is not expressed, since the B19p6 promoter is erythroid cell-specific. Detection of the heterologous gene product at levels at or below the level of untransduced cells confirms that the B19p6 promoter of the hybrid vector does not direct expression of the heterologous gene in non-hematopoietic cells.

The hybrid vectors of the present invention are useful for gene therapy. In particular, the vectors of the present invention can direct erythroid cell-specific expression of a desired gene, and thus are useful in the treatment of hemoglobinopathies.

It is contemplated in accordance with the present invention to use the hybrid vector in the treatment of a variety of diseases, including thalassemia, sickle-cell anemia, diabetes and cancer. The heterologous gene can be the normal counterpart of one that is abnormally produced or underproduced in the disease state, for example β-globin for the treatment of sickle-cell anemia, and α-globin, β-globin or γ-globin in the treatment of thalassemia. The heterologous gene can encode antisense RNA as described hereinabove. For example, α-globin is produced in excess over β-globin in β-thalassemia. Accordingly, β-thalassemia can be treated in accordance with the present invention by gene therapy with a vector in which the heterologous gene encodes an antisense RNA. The antisense RNA is selected such that it binds to a target sequence of the α-globin mRNA to prevent translation of α-globin, or to a target sequence of the α-globin DNA such that binding prevents transcription of α-globin DNA. In the treatment of cancer the heterologous gene can be a gene associated with tumor suppression, such as retinoblastoma gene, the anti-oncogene p53, or the gene encoding tumor necrosis factor.

The use of the hybrid vectors of the present invention for the treatment of disease involves transduction of HSC or progenitor cells with the hybrid vector. Transduction is accomplished by transfection with the vector or preparation of mature virions containing the hybrid vectors and infection of HSC or progenitor cells with the mature virions. Transduced cells are introduced into patients, e.g. by intravenous transfusion (see, for example, Rosenberg, 1990). HSC or progenitor cells are provided by obtaining bone marrow cells from patients and optionally enriching the bone marrow cell population for HSC. HSC can be transduced by standard methods of transfection or infected with mature virions for about one to two hours at about 37° C. Stable integration of the viral genome is accomplished by incubation of HSC at about 37° C. for about one week to about one month. The stable, site-specific integration and erythroid cell-specific expression is assessed as described above. After the transduced cells have been introduced into a patient, the presence of the heterologous gene product can be monitored or assessed by an appropriate assay for the gene product in the patient, for example in peripheral red blood cells or bone marrow of the patient when expression is erythroid cell-specific. As described hereinabove, the specific assay is dependent upon the nature of the heterologous gene product and can readily be determined by one skilled in the art.

For example, β-thalassemia represents a heterologous group of clinical syndromes that are inherited as mutated alleles of genes that encode the human β-globin chain. These mutations affect all aspects of β-globin gene expression including transcription, splicing, polyadenylation, translation and protein stability. The hallmark of β-thalassemia is the marked reduction or total absence of synthesis of normal adult hemoglobin (HbA; $\alpha_2\beta_2$). Despite significant advances in the understanding of basic underlying molecular mechanisms of β-thalassemia, treatment is limited to regular red blood cell transfusions and iron-chelation therapy. Treatment by bone marrow transplantation has also been attempted [Thomas et al. (1982) Lancet, ii, 227], but an effective cure has not been found.

Accordingly, the vectors of the present invention are useful in the treatment of β-thalassemia. An AAV-B19 vector is constructed in which the heterologous gene is the normal human β-globin gene, with the resulting AAV-B19-β-globin vector allowing parvovirus-mediated transfer, site-specific integration and erythroid cell-specific expression of the normal human β-globin gene in human hematopoietic cells.

Abnormal β-globin expression β-thalassemia may result in the overabundance of α-globin mRNA relative to β-globin mRNA. The present invention cannot only provide a normal β-globin gene, as described hereinabove, but can further be utilized to down-regulate the production of excess α-globin by providing a vector with an antisense RNA as the heterologous gene. An AAV-B19 hybrid vector is constructed in which the heterologous sequence encodes an antisense RNA which is sufficiently complementary to a region of the mRNA encoding the α-chain, such that it binds to and prevents translation of the α-globin mRNA, or to a region of the DNA encoding α-globin such that it binds to and prevents transcription of the α-globin gene. Hence, the present invention contemplates gene therapy for β-thalassemia comprising transduction of hematopoietic stem or progenitor cells with a hybrid vector encoding normal β-globin chains, or simultaneous transduction with a vector encoding a normal β-globin chain and a vector encoding an RNA antisense to α-globin mRNA or DNA. Alternately, a construction with more than one B19p6 promoter, as described hereinabove, permits coincident expression of β-globin and antisense α-globin. Accordingly, transduction with a single vector effects both the provision of a normal β-globin gene and the down-regulation of excess α-chains. More specifically, bone marrow cells are transfected with the subject vectors, and transduced cells are introduced, e.g. by intravenous transfusion, into a patient. The stable integration of the vector can be assessed by PCR or Southern blot analysis and the expression of the heterologous gene can be evaluated by assaying for the heterologous gene product in the patient's peripheral blood cells or bone marrow cells. As described previously, the particular assay depends upon the nature of the heterologous gene product.

The vectors of the present invention are also useful in conferring cell specific multidrug resistance. An AAV vector is contructed to contain a cell-specific promoter and a multidrug resistance gene, with the resulting vector allowing parvovirus-mediated transfer, site-specific integration and cell-specific expression of the mdr gene in a selected cell type. In a preferred embodiment, the vector is AAV-B19-mdr, and confers the multidrug resistance phenotype to erythroid cells.

Any of the numerous mdr genes known to confer the mdr phenotype is useful as the heterologous gene. The mdr genes are known to the ordinarily skilled artisan and are described, for example, by Roninson et al. (1991) in *Molecular and Cellular Biology of Multidrug Resistance in Tumor Cells* (ed. Roninson, Plenum Press, NY) 91–106. Accordingly, the present invention provides a method of conferring cell-specific multidrug resistance which comprises transducing cells with the hybrid vector of the present invention which contains a cell-specific promoter and an mdr gene. In a preferred embodiment, the present invention provides a method of conferring multidrug resistance to erythroid cells of a patient which comprises obtaining bone marrow or stem cells from a patient, transducing the bone marrow or stem cells with the AAV-B19 hybrid vector of the present invention which contains an mdr gene as the heterologous gene, and reintroducing the transduced cells into a patient. The expression of the mdr gene can be evaluated by assaying for the mdr gene product, i.e., P-glycoprotein, in the patient's peripheral blood cells or bone marrow cells. For example, P-glycoprotein can be detected by known immunologic assays with an antibody against P-glycoprotein. Such antibodies are known and available to the ordinarily skilled artisan, and are described, for example, by Meyers et al. (1989) *Cancer Res.* 49, 3209 and Georges et al. (1990) *Proc. Nat'l Acad. Sci. USA* 87, 152. The present method is particularly useful as an adjunct to cancer chemotherapy in that it effectively results in the protection of erythroid cells from the effects of chemotherapeutic agents targeted to other tissues.

Yet another aspect of the present invention provides a method for delivery of a pharmaceutical product, a protein or an antisense RNA in a mammal. Since the normal differentiation of these stem cells results in production of mature erythrocytes, the transduction of stem cells with the subject vector ultimately yields a population of circulating, enucleate vesicles containing the gene product. This method comprises transducing hematopoietic stem or progenitor cells with the hybrid vector of the present invention and introducing, e.g. by intravenous transfusion or injection, the transduced cells into a mammal. Transduction can be accomplished by transfecting cells with the hybrid vector by standard methods of infecting cells with mature AAV virions containing the hybrid vector at about 37° C. for about one to two hours. Stable integration of the recombinant viral genome is accomplished by incubating cells at about 37° C. for about one week to about one month. Transduced cells are recognized by assaying for expression of the heterologous gene, as described hereinabove. In this embodiment, the pharmaceutical product is encoded by the heterologous gene of the hybrid vector, and can be any pharmaceutical product capable of being expressed by the hybrid vector. Such products include α, β and γ-globin, insulin, GM-CSF, M-CSF, G-CSF, EPO, TNF, MGF, interleukins, the gene product of the retinoblastoma gene, p53 or adenosine deaminase. Therefore, the present invention can provide production of constitutive levels of heterologous gene products inside membrane vesicles, specifically red blood cells, for in situ treatment of disease. Optionally, the hybrid vector can further comprise a sequence which encodes a signal peptide or other moiety which facilitates the secretion of the gene product from the erythroid cell. Such sequences are well-known to one of ordinary skill in the art [see, for example, Michaelis et al. (1982) *Ann. Rev. Microbiol.* 36, 435] and can be inserted into the subject vectors between the promoter and coding region by methods described herein. This method can be used to treat a variety of diseases and disorders and is not limited to the treatment of hemoglobinopathies, since the heterologous gene is constitutively expressed and can be released from the red blood cell by virtue of a secretory sequence, or released when red blood cells are lysed in the liver and spleen.

The following examples further illustrate the present invention.

EXAMPLE 1

Site-Specific Integration of the Recombinant AAV Genome

Figure 4:
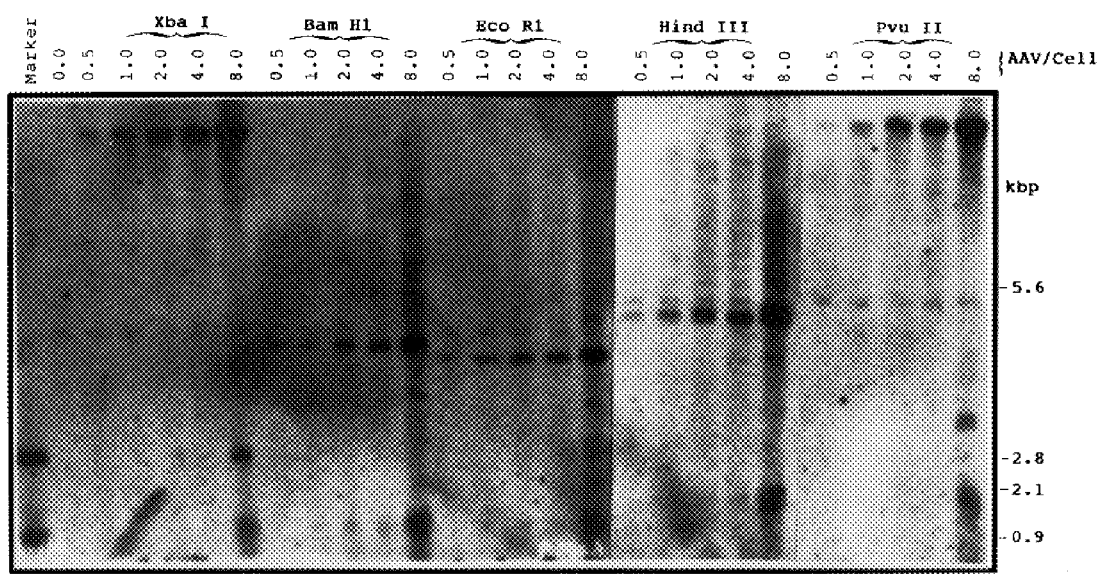
FIG. 4 demonstrates the site-specific integration of the wild-type AAV genome into normal human diploid chromosomal DNA by Southern blot analysis.

Site-specific integration of the AAV genome was confirmed by an approach in which normal human diploid fibroblasts (HDF) were either mock-infected, or infected with an increasing multiplicity-of-infection (moi) of wild-type AAV. Following multiple serial passage of these cells in culture, their total genomic DNA was isolated, digested with a variety of restriction endonucleases, and analyzed on Southern blots using an AAV-specific DNA probe. A representative Southern blot is presented in FIG. 4. Restriction enzymes are indicated at the top of the figure. The moi is indicated at the top of each lane, with 0.0 indicating mock-infection. The predominant single band of hybridization is evidence that the wild-type AAV genome integrates into normal human diploid cell chromosomal DNA in a site-specific manner. The target site was saturated only at very high moi of AAV, and no selection procedure was employed to select for cell populations that have the integrated provirus.

The site-specific integration of the recombinant AAV genome is demonstrated utilizing human bone marrow cells, which are the target cells for therapy of hemoglobinopathies.

Figure 5:
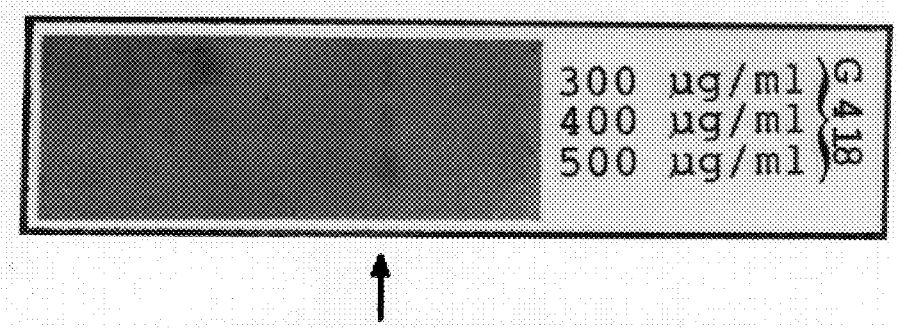
FIG. 5 demonstrates the site-specific integration of the recombinant AAV genome into normal human bone marrow cells by Southern blot analysis.

Bone marrow cells were obtained from hematologically normal volunteer donors, and low-density, mononuclear bone marrow (LDBM) cells were isolated by Ficoll-Hypaque density centrifugation. LDBM cells were infected with the recombinant AAV-Neo virions (vSV40-Neo), in which the Neo gene, under the control of the SV40 early promoter, is encapsidated into AAV particles, and incubated in the presence of various cytokines such as GM-CSF (1 ng/ml) and IL-3 (1 ng/ml) for 48 hours. The cells were incubated in liquid cultures in the presence of G418 at 37° C. for 10 days, their total genomic DNA was isolated, cleaved with BamHI, and analyzed on a Southern blot using a Neo-specific DNA probe as shown in FIG. 5. Concentration of G418 is indicated at the top of each lane. The single band of hybridization indicated by the arrow demonstrates that the recombinant AAV viral genome undergoes site-specific integration into human bone marrow cell chromosomal DNA.

EXAMPLE 2

Construction of Recombinant Plasmids pWP-7A and pWP-19

Figure 6A:
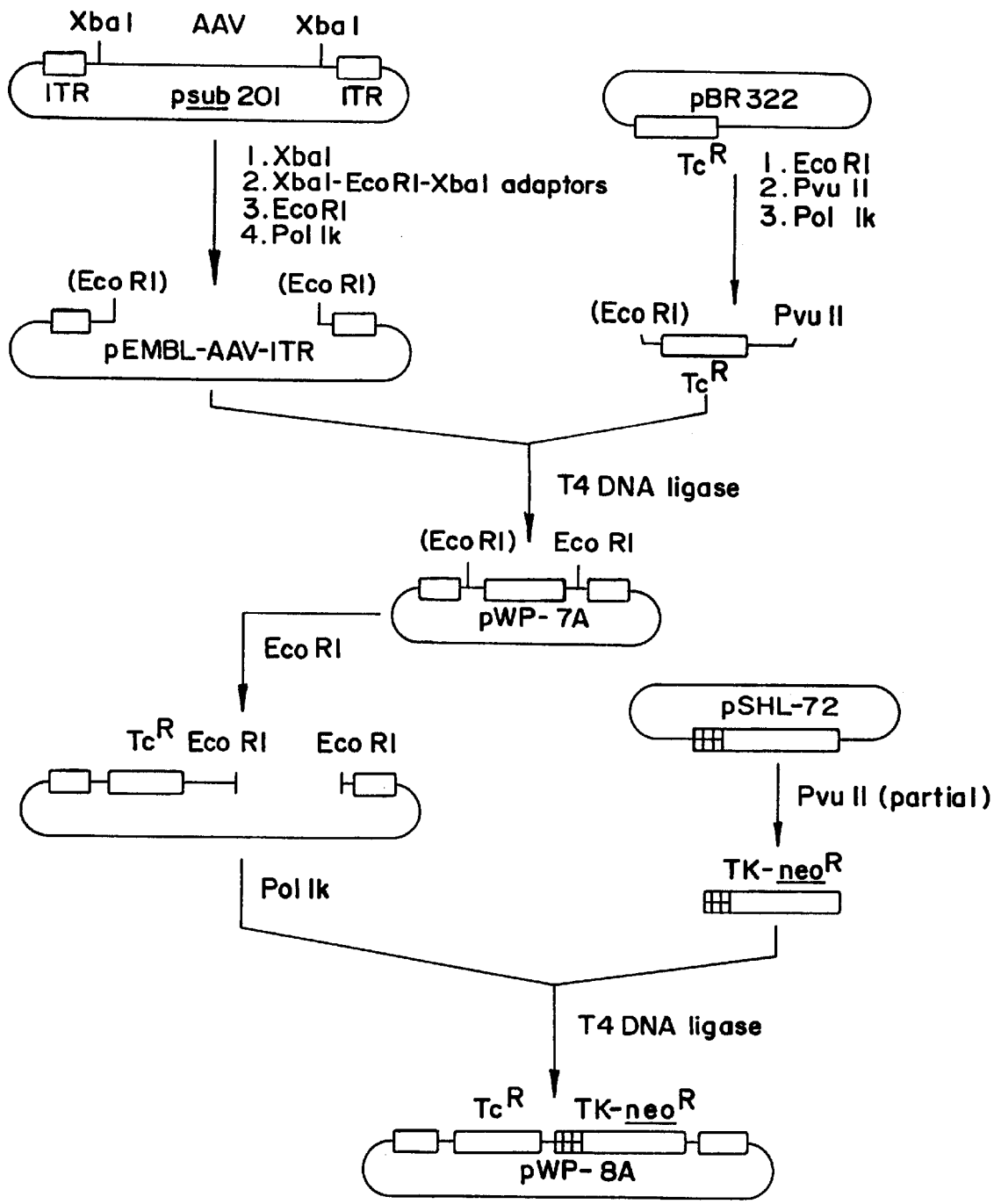
FIGS. 6A and B are diagrams of the construction of recombinant plasmids pWP-7A (Panel A) and pWP-19 (Panel B).
Figure 6B:
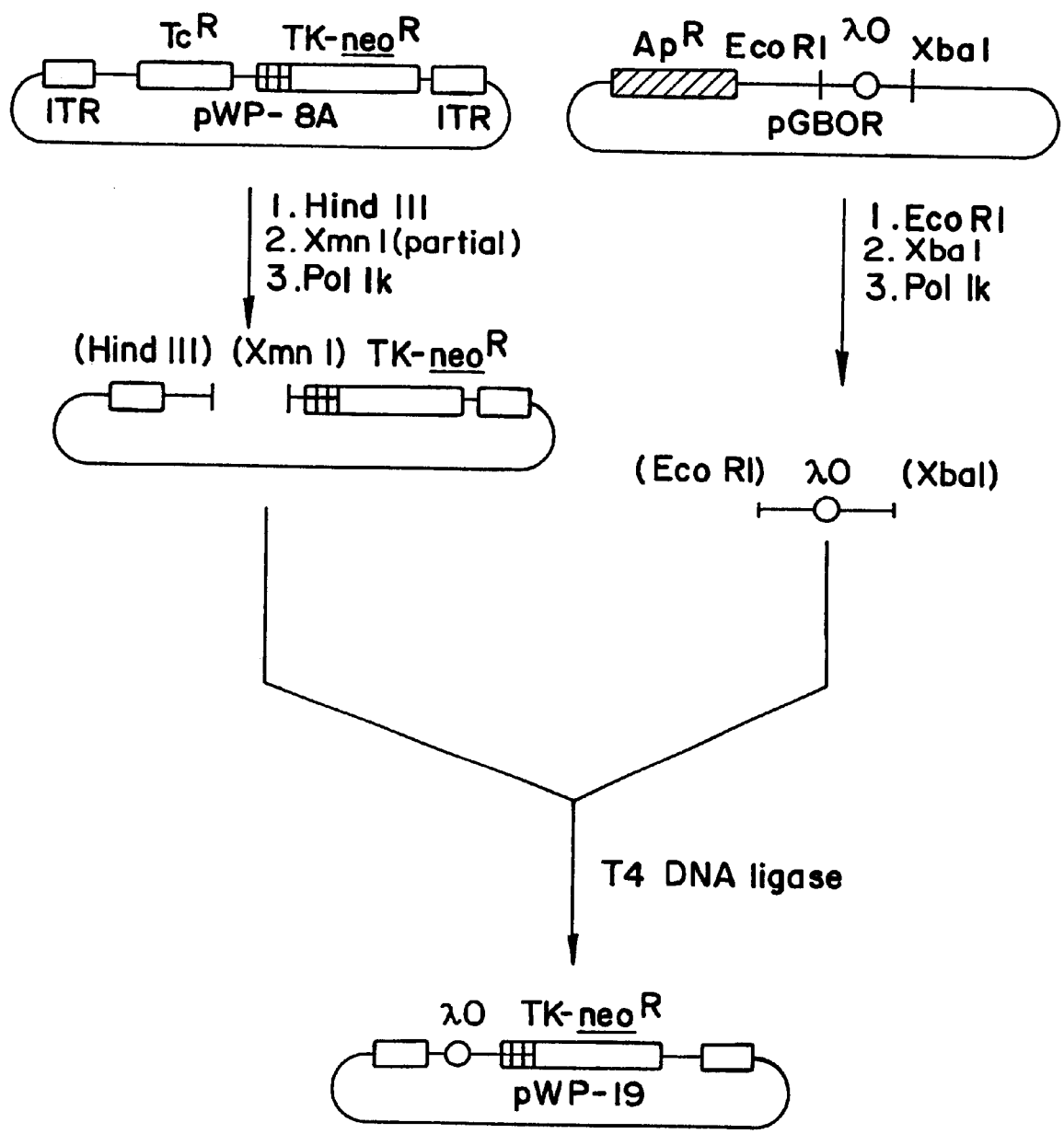

The general overall strategy used to construct the prototype plasmid vectors, designated pWP-7A and pWP-19, respectively, is depicted in FIG. 6. The XbaI sites in plasmid psub201 were converted to EcoR1 sites by ligating synthetic XbaI-EcoRI-XbaI adaptors as described by Srivastava et al. (1989) *Proc. Natl. Acad. Sci. USA* 86, 8078. The AAV coding region was removed following digestion with EcoR1, and the vector DNA containing the two AAV-ITRs was isolated from preparative agarose gels (Seth [1984] *Gene Anal. Tech.* 1, 99), and treated with PoIIk to generate blunt-ends. Similarly, pBR322 DNA was cleaved with EcoR1 and PvuII and a 2066 bp fragment containing the entire coding region of a gene for resistance to tetracycline ($Tc^r$) was also blunt ended with PoIIk. These two fragments were ligated and used to transform competent *E. coli* HB101 cells by the standard methods described in Sambrook et al. (1989) to generate a plasmid, designated pWP-7A. Since blunt-end ligation of DNA fragments containing repaired EcoR1 and PvuII ends regenerates an EcoR1 site, plasmid pWP-7A can be cleaved with EcoR1 downstream from the $Tc^R$ gene for cloning a gene or cassette of interest. The $neo^R$ gene under the control of the herpesvirus thymidine kinase (TK) promoter was isolated from plasmid pSHL-172 (Tratschin et al. [1985] *Mol. Cell. Biol.* 5, 3251) by partial digestion with PvuII, and blunt-end ligated with PoIIk-treated pWP-7A DNA. The resulting recombinant plasmid, designated pWP-8A, is shown in FIG. 6A. Plasmid pWP-19 was constructed as follows. Plasmid pWP-8A was linearized with HindIII, which cleaves at the 51 end of the $Tc^R$ gene, and partially digested with XmnI to remove the $Tc^R$ gene. A plasmid pGBOR which contains a gene for resistance to ampicillin ($Ap^R$) and the bacteriophage lambda operator (OR1/OR2;λo) sequences (Samulski et al. [1991] *EMBO J.* 10, 3941) was cleaved with EcoR1 and XbaI and the fragment containing the λo sequence was blunt-end ligated with PoIIk-treated pWP-8A DNA described above. The resulting recombinant plasmid pWP-19 is shown in FIG. 6B.

The plasmid vectors pWP-7A and pWP-19 are useful for constructing recombinant AAV genomes because direct insertion of an insert of interest is possible in both, and the presence of the built-in $neo^R$ gene in pWP-19 provides a strong selectable marker in human cells. The plasmid vector pWN-1 is particularly useful because it offers several features. In bacterial cells, these include: 1) The availability of a variety of cloning sites (EcoR1, BamH1, SacI, KpnI, XbaI, SalI, AccI, HincII, PstI, SphI and HindIII), including the NdeI site; 2) AAV-ITRs which are well separated from the cloning sites; and 3) the use of $Tc^2$ as well as $Ap^R$ as selectable markers. In mammalian cells, following transfection in the presence of the AAV helper plasmid and Ad, the insert of interest, which is now flanked by the two AAV-ITRs in their proper orientation (see FIG. 7), can be efficiently rescued from the $Tc^R$ gene followed by DNA replication and packaging in the AAV progeny virions.

Whereas plasmid pWP-7A is useful for cloning inserts up to 2.5 kb in size at the unique EcoR1 site, plasmid pWP-19 offers a built-in $neo^R$ marker gene as well as a number of cloning sites such as BamH1, SacI and KpnI, and insert up to 2.6 kb in size can be inserted between the two AAV-ITRs.

EXAMPLE 3

Construction of Recombinant Plasmid pWN-1

Figure 7:
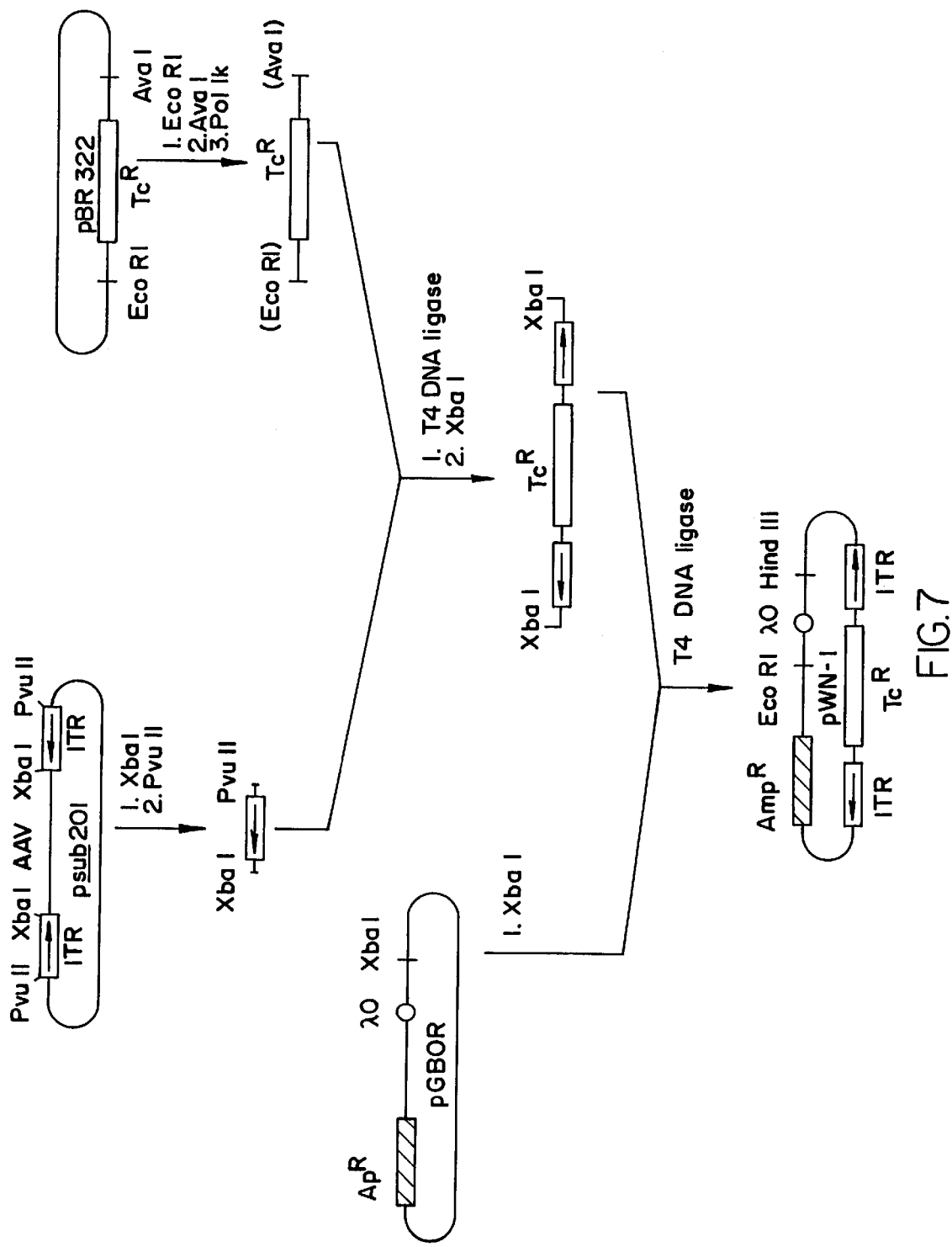
FIG. 7 is a diagram of the construction of recombinant plasmid pWN-1.

The strategy to construct the recombinant plasmid pWN-1 is shown in FIG. 7. Briefly, psub201 plasmid DNA was digested to completion with XbaI and PvuII, and a 191-bp XbaI-PvuII fragment containing the entire AAV-ITR sequence was isolated as described in Example 2. Similarly, pBR322 plasmid DNA was cleaved with EcoR1 and AvaI to isolate a 1425-bp fragment that contains the $Tc^R$ gene but lacks the origin of DNA replication ("ori") sequence. This fragment was treated with PoIIk to generate blunt ends. Blunt-ended EcoR1-AvaI fragment was mixed with a large excess of the XbaI-PvuII fragment containing the AAV-ITR, blunt-end ligated using T4 DNA ligase, and then digested exhaustively with XbaI. This resulted in the production of the $Tc^R$ gene flanked by a single AAV-ITR at each end but in the opposite orientation (see small arrows in boxed ITRs). This fragment was subsequently ligated at the unique XbaI site in plasmid pGBOR described above, and $Tc^R$ was used to select for the recombinant plasmid pWN-1.

EXAMPLE 4

Rescue and Replication of a Cloned Insert from Recombinant AAV-Based Plasmids

Figure 8A:
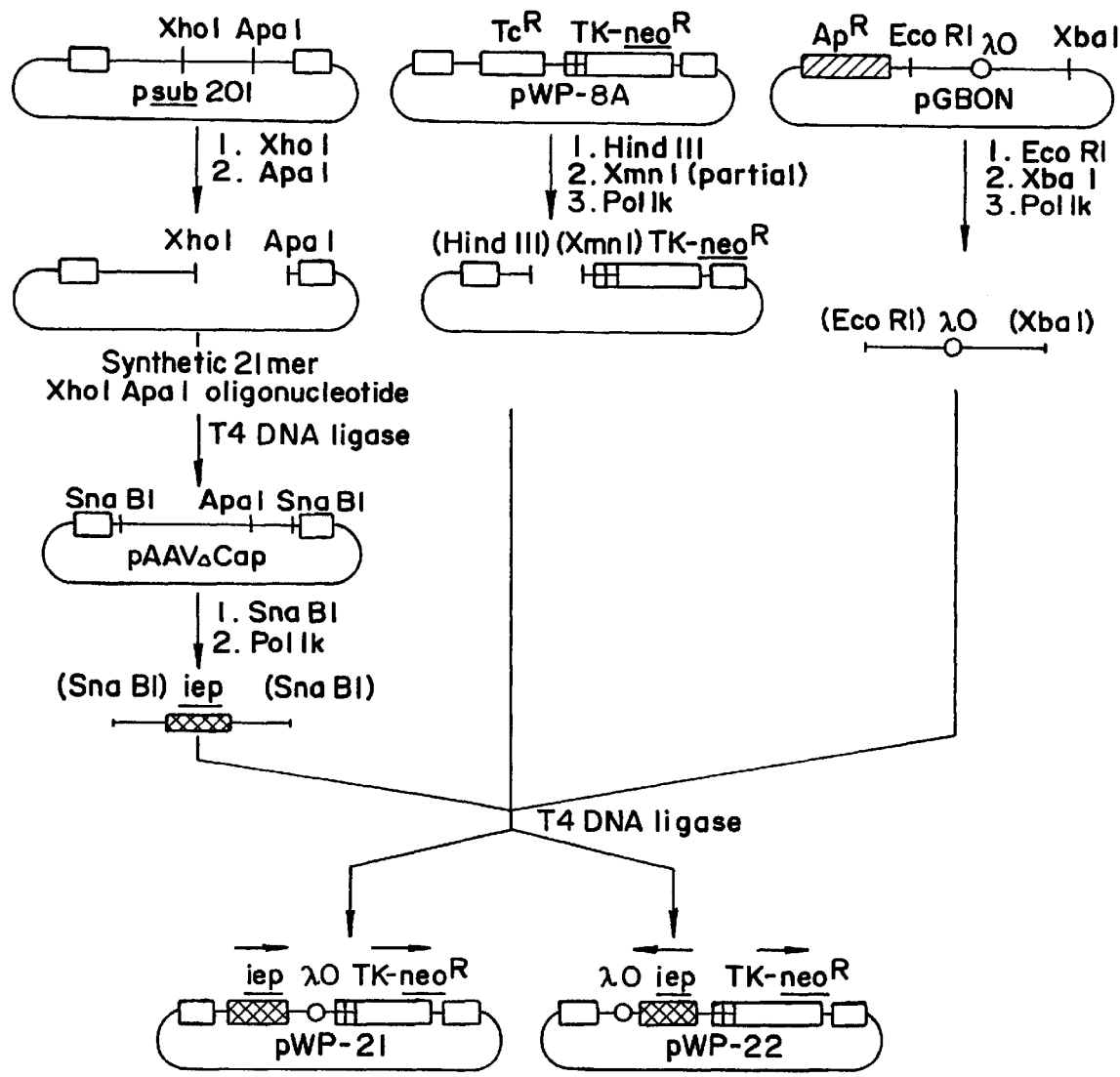
FIGS. 8A and B are diagrams of the construction of recombinant plasmids pWP-21 and pWP-22 (Panel A) and pWP-16 and pWP-17 (Panel B).
Figure 8B:
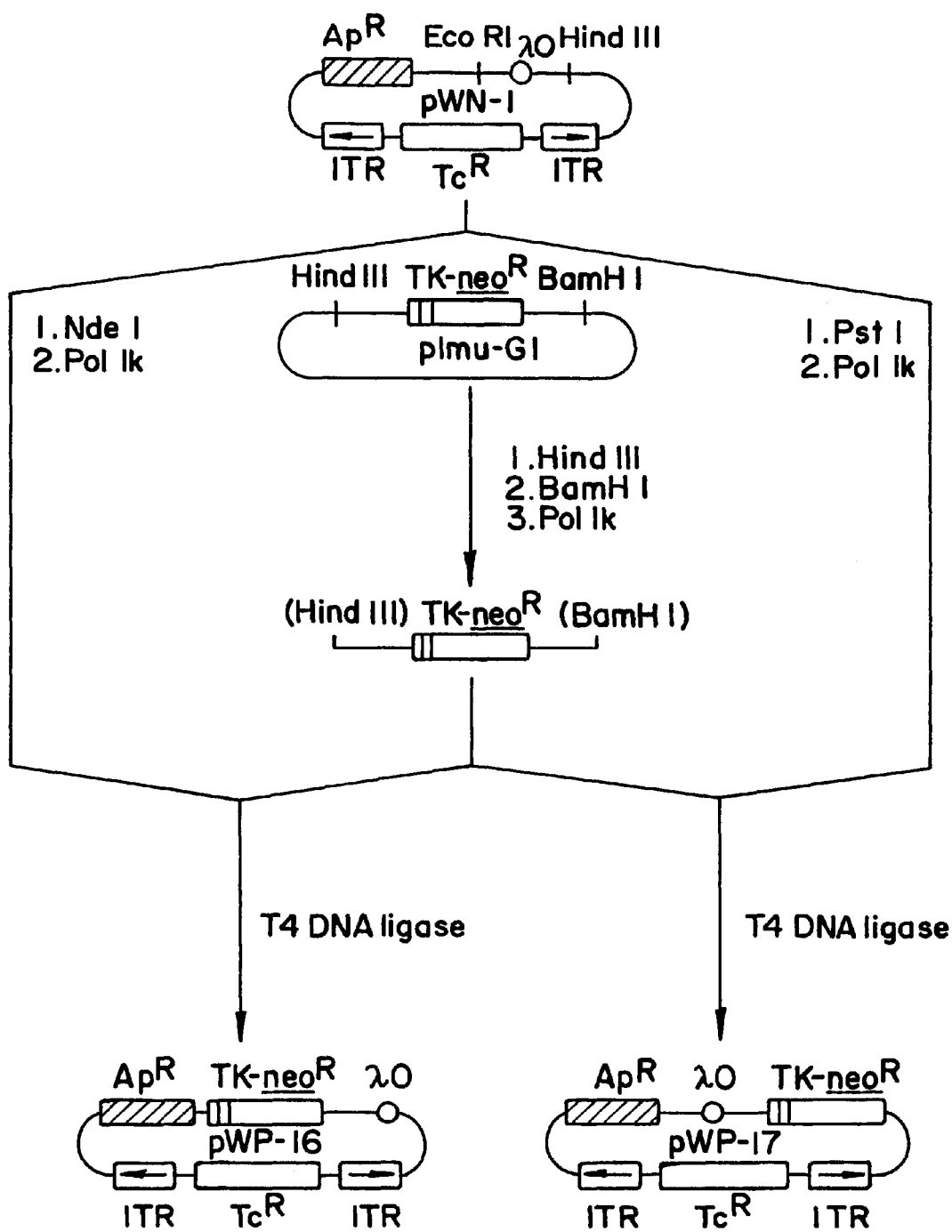

DNA sequences flanked by the two AAV-ITRs can be rescued from the recombinant plasmids of Examples 2 and 3 following transfection in human cells in the presence of the AAV and Ad proteins as a prelude to successful packaging of these genes into mature AAV virions. The insert size between the two AAV-ITRs in plasmid pWP-8A is similar to that of the wt AAV genome. The AAV-rep gene the parent plasmid psub201, as well as the λ OR1/OR2 sequences from plasmid pGBOR were isolated and inserted in plasmid pWP-19 by the strategy shown in FIG. 8A. Two recombinant plasmids, pWP-21 and pWP-22, were generated which contain the AAV-rep gene in different orientations with respect to the $neo^R$ gene. These plasmids are depicted in FIG. 8A. Similarly, the insert size between the two AAV-ITRs in plasmid pWN-1 was increased by inserting the $neo^R$ gene either at the NdeI site or at the PstI site to generate two recombinant plasmids, pWP-16 and pWP-17, respectively, which are shown in FIG. 8B.

Figure 9:
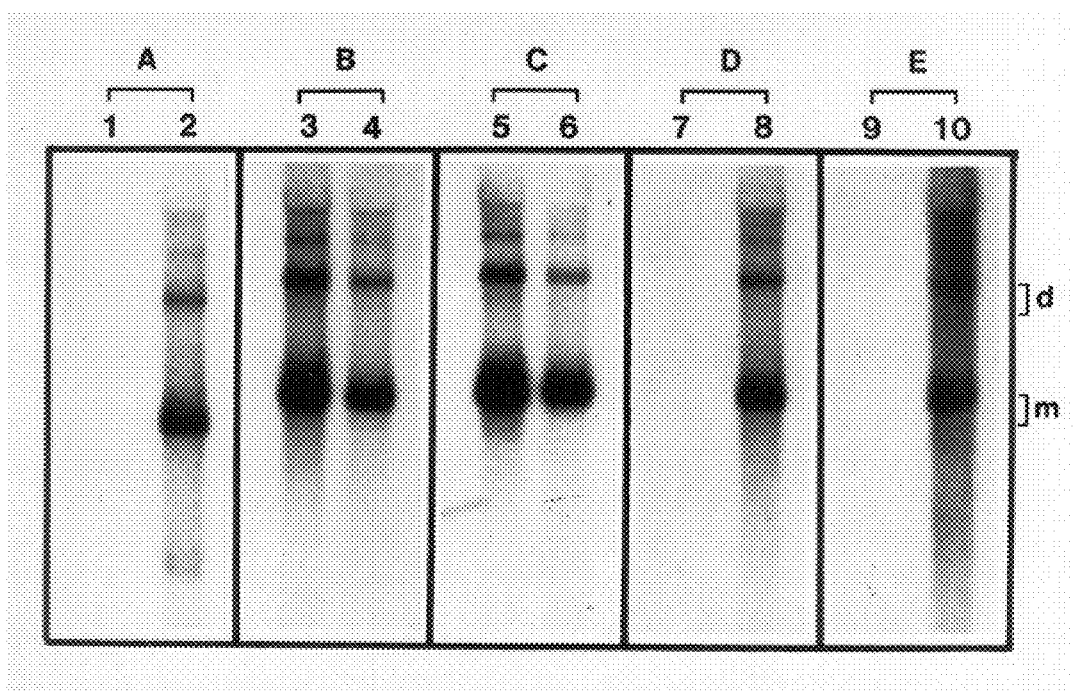
FIGS. 9A–9E demonstrate Southern blot analysis of rescue and replication of the recombinant $neo^r$ gene in human cells. Panel A: Rescue from plasmid pWP-8A; Panel B: Rescue from plasmid pWP-21; Panel C: Rescue from plasmid pWP-22; Panel D: Rescue from plasmid pWP-16; Panel E: Rescue from plasmid pWP-17. Recombinant plasmids were transfected separately in adenovirus-infected human KB cells (Lanes 1, 3, 5, 7, 9), or co-transfected with pAAV/Ad helper plasmid (Lanes 2, 4, 6, 8, 10). m and d denote the monomeric and dimeric forms, respectively, of the recombinant AAV DNA replicative intermediates.

Plasmids pWP-8A, pWP-21, pWP-22, pWP-16 and pWP-17 were either transfected alone, or co-transfected with the AAV helper plasmid (pAAV/Ad) separately, in Ad-infected human KB cells (Samulski et al. [1989] *J. Virol.* 63, 3822; Srivastava et al. [1989]; Srivastava [1990] *Blood* 76, 1997). Low $M_r$ DNA samples isolated by the method described by Hirt (1967) *J. Mol. Biol.* 26, 365, were digested with DpnI and analyzed on Southern blots (Southern [1975] *J. Mol. Biol.* 98, 503) using a neo-specific DNA probe as previously described (Samulski et al. 1989). The results are presented in FIG. 9. No rescue/replication of the recombinant $neo^R$ gene from plasmid pWP-8A occurred in the absence of the pAAV/Ad helper plasmid (Lane 1); successful rescue and replication indeed occurred when the AAV-Rep proteins were supplied in trans (Lane 2), as detected by the presence of the characteristic monomeric and dimeric replicative intermediates of the recombinant AAV genome. Similarly, rescue and replication occurred from plasmids pWP-21 (Lanes 3 and 4), and pWP-22 (Lanes 5 and 6) even in the absence of the helper plasmid because these plasmids contain the AAV-rep gene in cis. Rescue and replication from plasmids pWP-16 and pWP-17 also occurred, but only in the presence of the AAV helper plasmid (Lanes 8 and 10).

Following rescue and replication, the $neo^R$ gene could also be packaged into mature AAV progeny virions in presence of the AAV-Cap proteins. The recombinant AAV progeny virions were biologically active and infectious. For example, recombinant AAV-neo virions were used to transduce and stably integrate the $neo^R$ gene in a variety of diploid and polyploid human cells. The transduced $neo^R$ gene was biologically active, as determined by gene expression analyses on Northern blots, as well as by ready isolation of clonal populations of human cells that were resistant to geneticin.

EXAMPLE 5

Construction of an AAV-B19 Hybrid Parvovirus Cloning and Expression Vector

Figure 10:
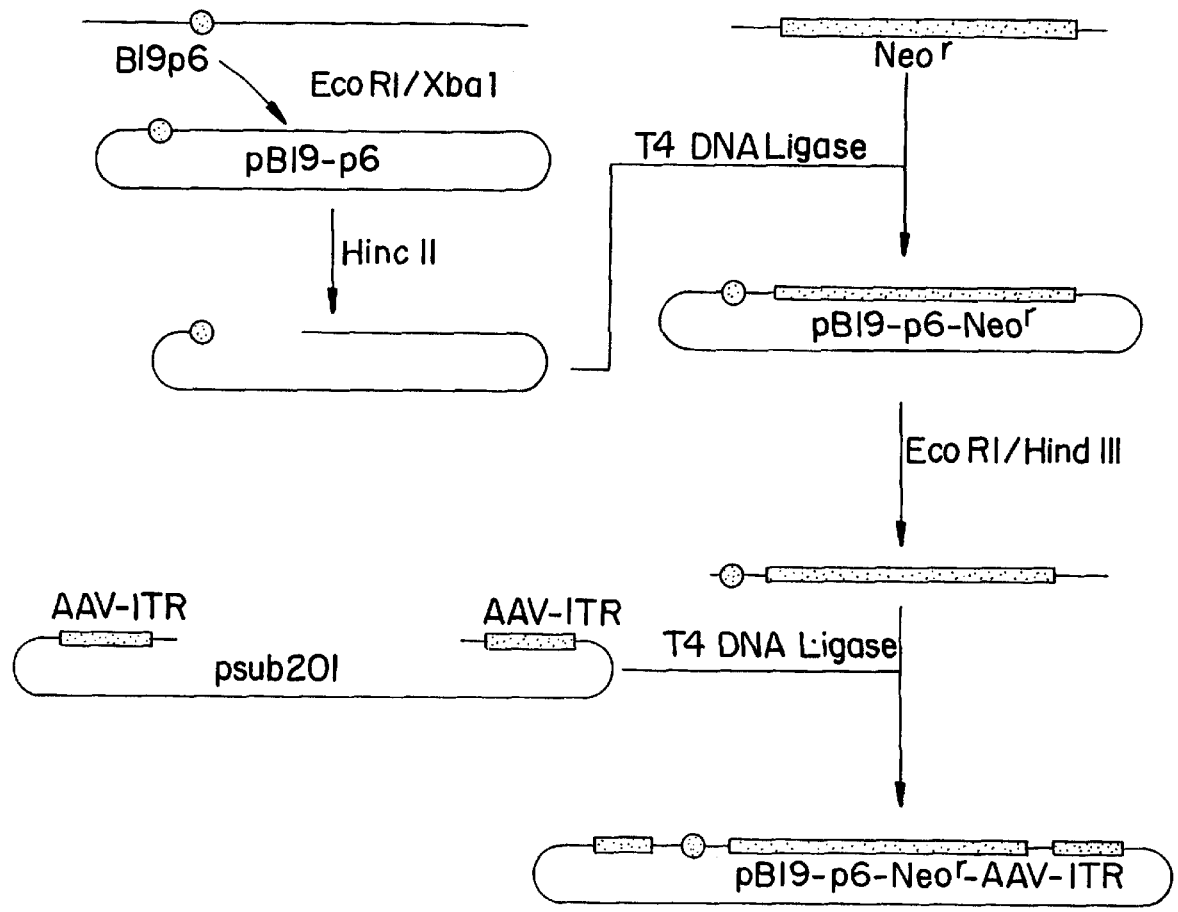
FIG. 10 is a diagram of the construction of a hybrid vector in which the neomycin resistance ($Neo^r$) gene is under the control of the B19p6 promoter.

A hybrid vector containing the AAV-ITRs the B19p6 promoter and the neo$^r$ gene as the heterologous gene was constructed as follows. The general strategy for the construction of this vector, designated pB19-p6-Neo$^r$-AAV-ITR, is shown in FIG. 10.

A near full-length B19 DNA clone (for example pYT104v in which B19 is downstream of the bacteriophage SP6 promoter) was cleaved with SacI and DraI, and the small DNA fragment that contains the left ITR was discarded. Following blunt-end re-ligation of the larger fragment, the plasmid DNA was cleaved with EcoRI and XbaI to isolate the 280 bp fragment that contains the entire 5' non-coding region and the p6 promoter of B19. This fragment was cloned into the EcoRI-XbaI sites of pUC19 to generate a plasmid pB19p6. This plasmid was cleaved with HincII which digests the B19 DNA downstream from the p6 promoter and also the pUC19 DNA in the multiple cloning site. The bacterial Neo$^r$ gene (Tratschin et al., 1985) was blunt-end ligated downstream from the B19p6 promoter between the two HincII sites to generate the plasmid pB19p6-Neo$^r$. This plasmid was digested with EcoRI and HindIII and the B19p6-Neo insert was isolated and ligated between the two AAV-ITRs of XbaI digested psub201. The vector was packaged into mature AAV virions (vB19-Neo) by cotransfection of adenovirus infected cells with pAAV/Ad, which contains the AAV-coding sequence and the adenovirus type 5 terminal sequences (Samulski et al. 1989).

EXAMPLE 6

Recombinant Parvovirus-Mediated Transfer of Bacterial Neo$^r$ Gene in Human Hematopoietic Stem Cells Human hematopoietic stem cells were isolated from normal volunteer donors followed by sorting with monoclonal antibodies against the human CD34 and DR antigens according to the method of Lu et al. (1987) *J. Immunol.* 139, 1823 to produce a CD34$^+$DR$^-$ cell population. This cell population is known to contain several classes of primitive human hematopoietic progenitor cells including colony forming unit-blast cells (CFU-B1), high-proliferative potential colony forming cells (HPP-CFC), and cells responsible for initiating long-term hematopoiesis in vitro (LTBMIC).

Figure 11A:
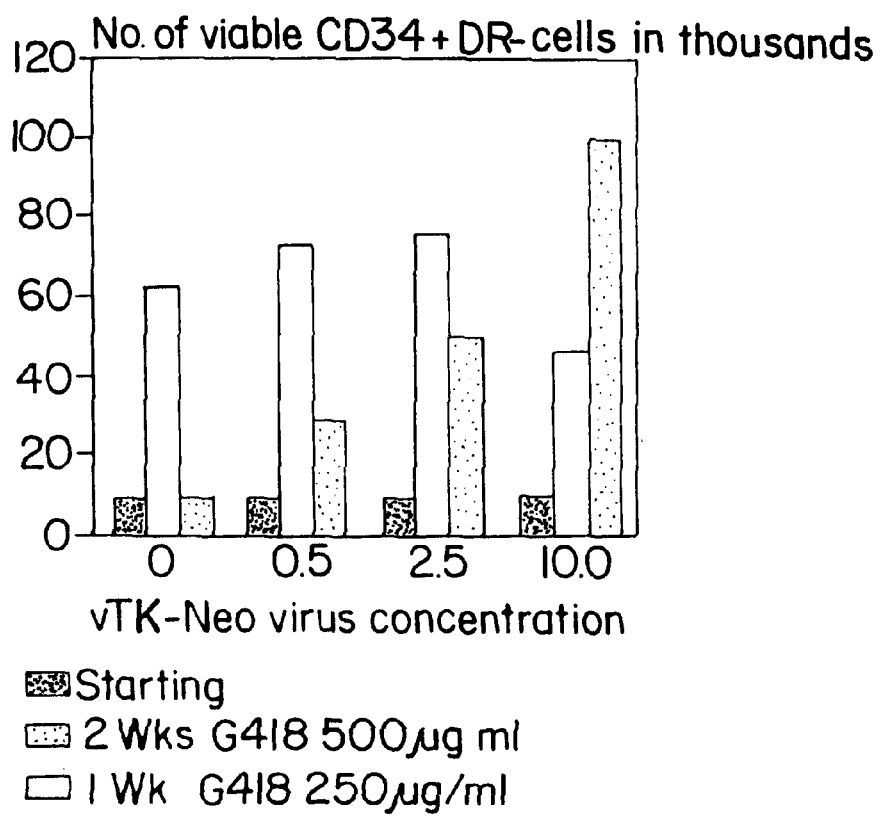
FIGS. 11A and 11B are graphs depicting cell viability after AAV-mediated transfer of $Neo^r$ to human hematopoietic stem cells. Panel A illustrates $Neo^r$ gene expression under the control of the TK promoter. Panel B illustrates $Neo^r$ gene expression under the control of the B19p6 promoter.
Figure 11B:
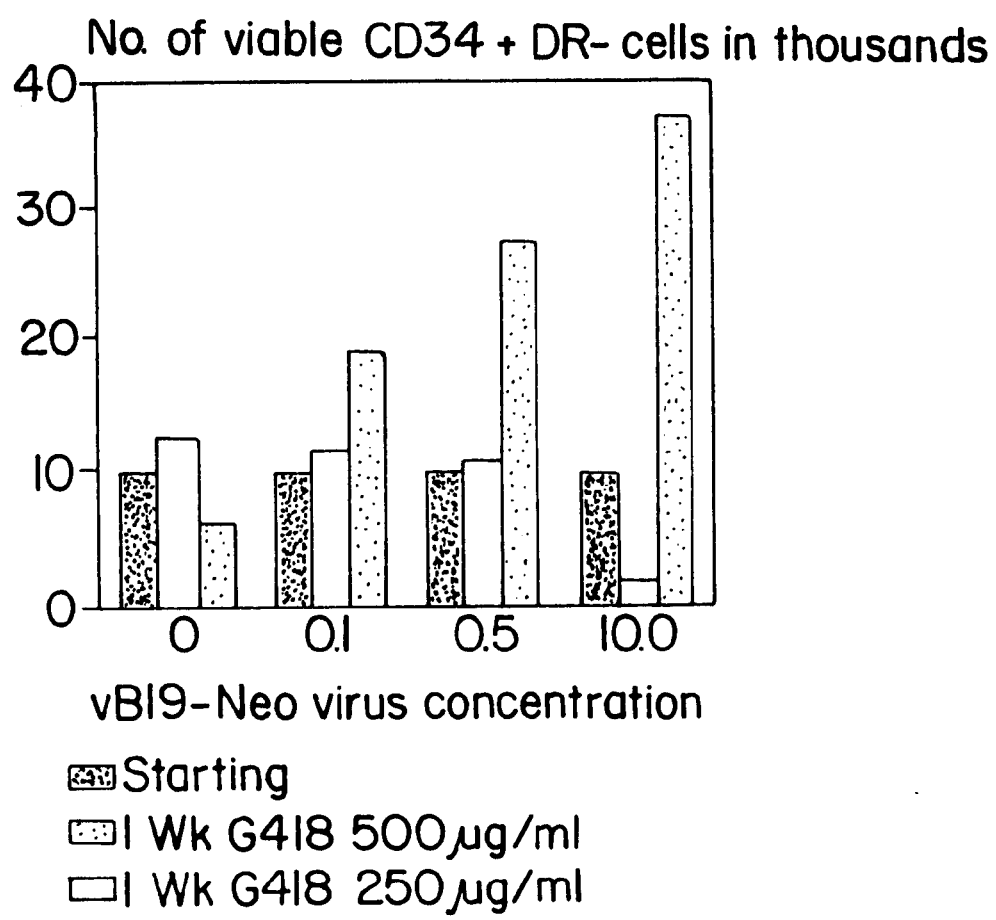

Approximately $1 \times 10^3$ CD34$^{+DR-}$ cells isolated from two different donors were either mock-infected, or infected at varying moi with vTK-Neo or vB19-Neo virions. (vTK-Neo is recombinant AAV virion containing the Neo$^r$ gene under the control of the thymidine kinase (TK) promoter). Cells were incubated at 37° C. for one week in the presence of the cytokines interleukin-3 (1 ng/ml), granulocyte macrophage colony stimulating factor (1 ng/ml), and a factor for c-kit ligand termed mast cell growth factor (50 ng/ml). G418 was added at a final concentration of 250 $\mu$g/ml. The total number of viable cells was counted following one-week exposure to the drug. The concentration of G418 was then increased to 500 $\mu$g/ml, and viable cell counts were obtained after two weeks for vTK-Neo-infected cells, and after one week for vB19-Neo-infected cells. These data are shown in FIG. 11.

Exposure to vTK-Neo virions resulted in a nearly 10-fold increase in the G418-resistant hematopoietic cell population compared with mock-infected cells, whereas the exposure to the vB19-Neo virions resulted in approximately 4-fold increase at the highest moi of the virions compared with mock infected cells. These results demonstrate that the B19p6 promoter is active in cell populations enriched for HSC, albeit at a lower level compared with the TK promoter.

EXAMPLE 7

Evaluation of Tissue-Specificity of the B19p6 Promoter

Non-erythroid cells were infected to determine whether the B19p6 promoter in the hybrid constructions had become indiscriminate or had maintained its erythroid specificity.

Human KB cells were either mock-infected or infected separately with equivalent moi of vTK-Neo and vBl9-Neo. At 48 hours post-infection cells were exposed to various concentration of G418. Following a 14-day incubation period at 37° C., the approximate numbers of G418-resistant colonies were enumerated. A colony is defined as a group of eight or more cells. These data are presented in Table 1, and demonstrate that under conditions of viral infection, the B19p6 promoter retains its erythroid-specificity.

TABLE 1

Approximate Numbers of G418-Resistant Colonies in KB Cells Transduced with AAV-Neo Virions

| Recombinant virus | 200 $\mu$g/ml G418 | 400 $\mu$g/ml G418 | 600 $\mu$g/ml G418 |
| --- | --- | --- | --- |
| 1. None | 10–20 | 0 | 0 |
| 2. vTK-Neo | TMTC* | 100–200 | 50–100 |
| 3. vB19-Neo | 10–20 | 0 | 0 |

*TMTC = Too many to count

EXAMPLE 8

Construction of Parvovirus Vectors with an Erythroid-Specific Enhancer

Figure 12:
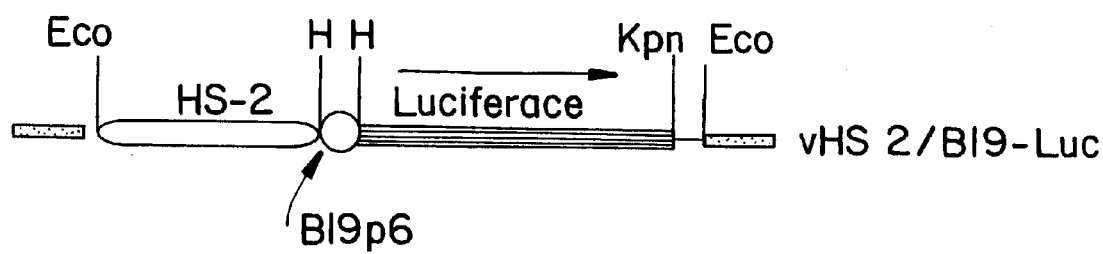
FIG. 12 depicts recombinant AAV vectors of the present invention containing selectable genes under the control of B19p6 promoter and a human erythroid-specific enhancer (HS-2).

In order to further increase the tissue-specific expression directed by the B19p6 promoter, the DNaseI-Hypersensitive Site-2 (HS-2) of the Locus Control Region (LCR), (Tuan et al. (1985) *Proc. Natl. Acad. Sci. USA* 82, 6384), an erythroid-specific enhancer, was inserted into the hybrid vectors of the present invention. As diagrammed in FIG. 12, the HS-2 gene is inserted upstream of the B19p6 promoter and luciferase gene to provide the vector vHS2/B19-Luc. Restriction sites used to facilitate vector construction are shown in FIG. 12. These constructs were packaged into mature AAV virions.

EXAMPLE 9

Figure 13:
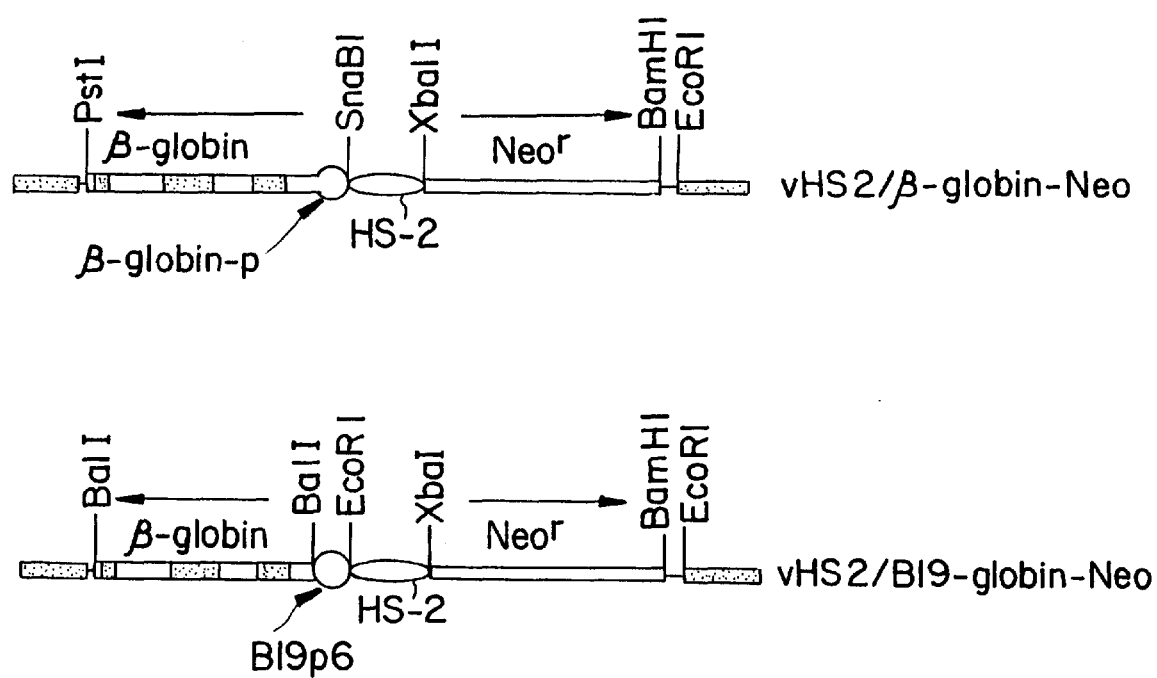
FIG. 13 depicts the recombinant AAV vectors of the present invention which express the human β-globin gene and the $Neo^r$ gene.

Construction of Parvovirus Vectors Containing the Normal Human β-Globin Gene In order to provide vectors for gene transfer in clinical cases of β-thalassemia and sickle-cell anemia, two plasmid vectors that contain the normal human β-globin gene were constructed and packaged into recombinant AAV virions. The pHS2/β-globin-Neo construct contains the β-globin promoter and the upstream HS-2 enhancer, along with the Neo$^r$ gene under the control of the TK promoter, and the pHS2/B19-globin-Neo construct also contains the B19p6 promoter. These constructs are shown in FIG. 13.

The pHS2/β-globin-Neo vector was constructed as follows. A plasmid (pWP19) was constructed that contains the Neo[r] gene under the TK promoter between the two AAV-ITRs. pWP19 was linearized with Sac1. A SnaBI-PstI fragment containing the genomic clone of the human β-globin gene was ligated, in reverse orientation, upstream of the TK promoter. The resulting plasmid was linearized by digestion with KpnI, and a HindIII-XbaI fragment containing the HS2 enhancer was ligated upstream of the β-globin promoter.

The pHS2/B-19-globin-Neo vector was constructed as follows. First the HindIII-XbaI fragment containing the HS2 enhancer was cloned upstream of the β19p6 promoter in the plasmid pB19p6 by linearizing it with EcoRI. The HS2-B19p6 fragment was isolated by digesting this plasmid with PvuII and HincII. The PvuII-HincII fragment was ligated to pWP19 plasmid linearized with SacI. Second, the β-globin coding region lacking the β-globin promoter was excised by digesting the plasmid with NcoI and PstI. This NcoI-PstI fragment was ligated to the plasmid described above by linearizing it with KpnI.

Similarly, vectors containing the human α-globin gene in both orientations were constructed and packaged into recombinant AAV virions. A HinfI-PvuII fragment of the cloned a-globin gene (Liebhaber, 1980) was ligated downstream from the B19p6 promoter following linearization of the pB19p6 plasmid DNA. The resulting plasmid was linearized with Fsp1, and ligated with the pWP19 plasmid at the Sac1 site prior to packaging into the AAV virions.

EXAMPLE 10

AAV Tranduction of Human Cells with the Multidrug Resistance Gene

To assess the ability of AAV vectors to confer the multidrug resistance phenotype to drug sensitive human cells, drug sensitive human KB cells are transduced with the AAV vector containing an mdr gene under the control of the thymidine kinase promoter. The expression of the mdr phenotype is assessed by detection of P-glycoprotein with an antibody specific for this protein. Further, the ability of the transduced cells to reduce intracellular accumulation of certain anti-tumor drugs is evaluated by culturing transduced cells in a series of tissue culture media containing step-wise concentration increases of the selected drug. An increase in viability of transduced cells relative to control (untransduced) cells is indicative of expression of the mdr gene.

To evaluate the ability of the AAV vectors of the present invention to confer cell-specific multidrug resistance, both erythroid and non-erythroid (e.g. drug sensitive KB) cells are transduced with the AAV vector containing an mdr gene under the control of the B19p6 promoter (AAV-B19p6-mdr). KB cells are transduced and assessed as described above. Since the B19p6 promoter directs erythroid cell-specific expression, the mdr gene is not expressed by transduction of KB cells with AAV-B19p6-mdr.

The ability of AAV-B19p6-mdr to confer erythroid cell-specific multidrug resistance is assessed as follows. Bone marrow is removed from a patient, enriched to CD34[+] cells and transduced with AAV-B19p6-mdr. Primary cultures are then established and maintained until focal colonies can be transferred to tissue culture trays. Outgrowth of such colonies permits the assessment of resistance to a range of anti-tumor drugs.

The AAV-B19p6-mdr vector is useful in cancer chemotherapy. For example, bone marrow is removed from the iliac creast of a cancer patient, and enriched for CD34[+] cells. Enriched cells are transduced by AAV-B19p6-mdr and reinfused into the patient.

The B19p6 promoter can be substituted by other cell-specific promoter elements to permit expression of the multidrug resistance phenotype in other cell lineages.

EXAMPLE 11

Cells of a human erythroleukemia cell line, K562 (ATCC CCL-243) were infected with vHS2/B19-globin-Neo (see Example 9 and FIG. 13) to assess the ability of the vector to provide expression of the β-globin gene in a host cell which exhibits no β-globin gene expression.

Figure 14:
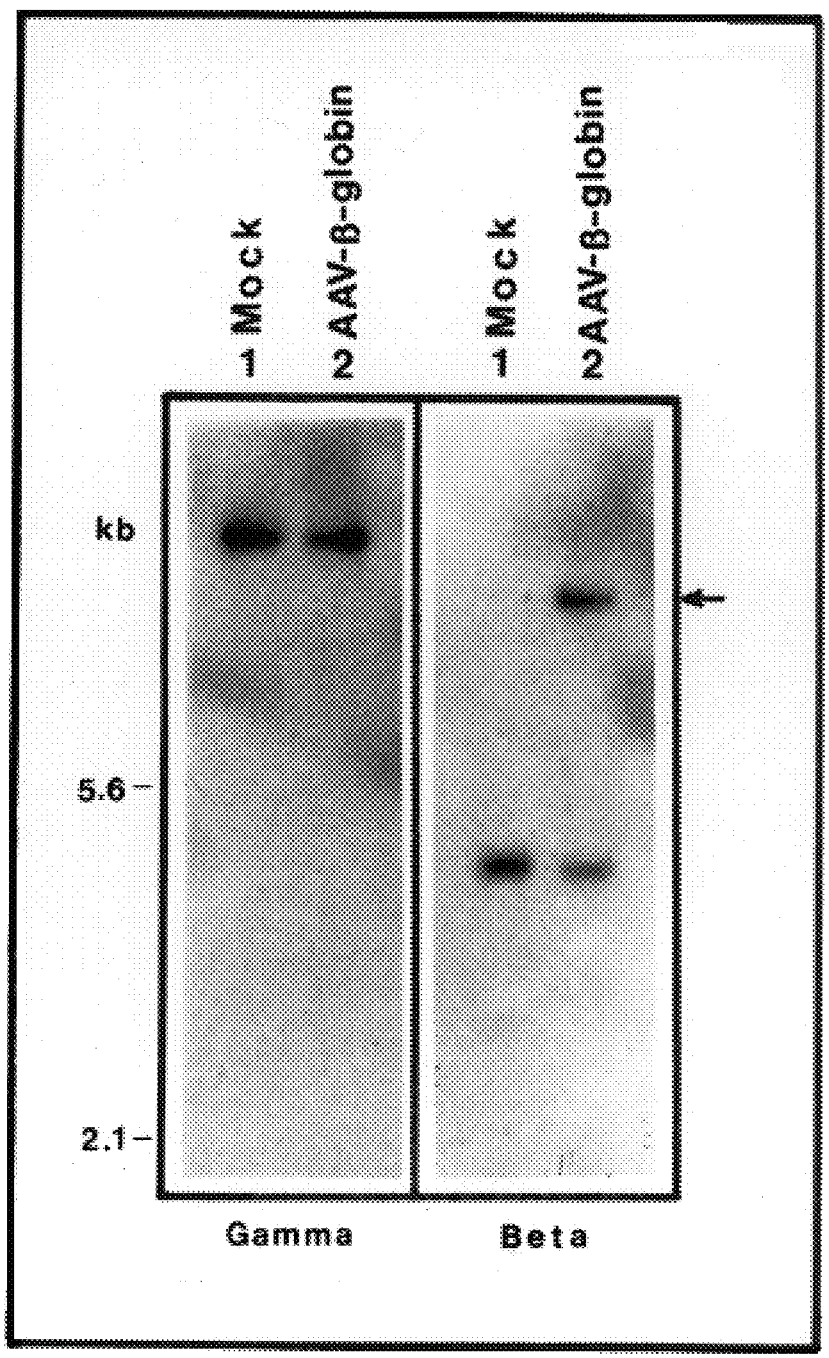
FIG. 14 provides a Souther blot of DNA isolated from vHS2/β-globin-Neo infected K562 cells.

K562 cells were either mock-infected or infected separately with equivalent moi of vHS2/B19.-globin-Neo and vHS2/β-globin-Neo. DNA of infected cells was isolated, digested with NcoI, and subjected to Southern blot analysis. FIG. 14 provides a Southern blot in which Lane 1 corresponds to DNA isolated from mock-infected cells, and Lane 2 corresponds to DNA isolated from cells infected with vHS2/β-globin-Neo. The blots were probed with a γ-globin probe (left panel) and a β-globin probe (right panel). The arrow denotes the transduced allele of the β-globin gene in K562 cells infected with vHS2/β-globin-Neo. Similar results were obtained for K562 cells infected with vHS2/B19-globin-Neo.

Figure 15:
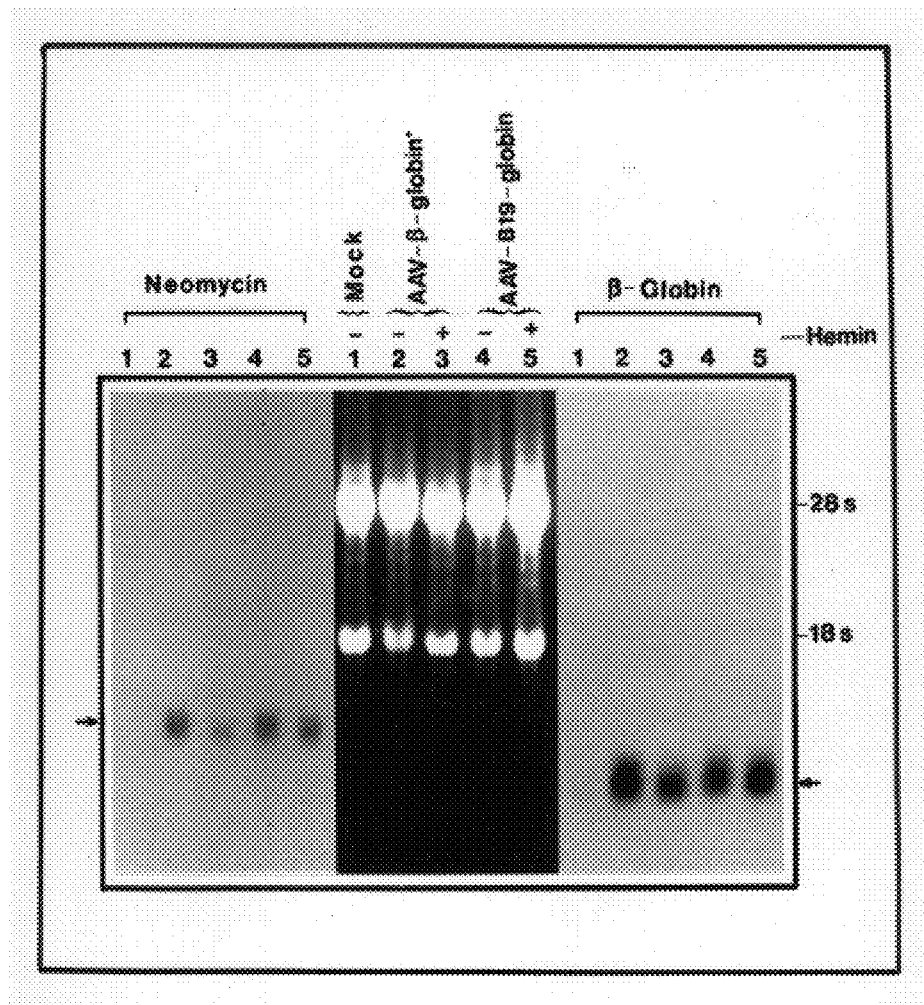
FIG. 15 provides a Northern blot of RNA from K562 cells infected with vHS2/β-globin-Neo and vHS2/B9-globin-Neo.

The β-globin gene is present but not expressed in K562 cells. Northern blots of total RNA from the mock-infected and infected cells described above were probed with a neomycin probe (FIG. 15, left panel) and a β-globin probe (FIG. 15, right panel). The center panel of FIG. 15 presents an ethidium-bromide stained gel. Lane 1 in each panel represents RNA from mock-infected cells; Lanes 2 and 3 correspond to RNA from vHS2/β-globin-Neo infected cells; Lanes 4 and 5 correspond to RNA from vHS2/B19-globin-Neo infected cells. Plus and minus signs indicate the presence or absence, respectively, of hemin, an inducer of γ-globin which appeared to have no effect on β-globin expression. The Northern analysis indicates that the β-globin gene is expressed in K562 cells infected with vHS2/β-globin-Neo and vHS2/B19-globin-Neo, but not in mock-infected cells.

---

What is claimed:

1. An expression vector for site-specific integration and cell-specific gene expression comprising two inverted terminal repeats of adeno-associated virus 2 and at least one cassette comprising a promoter capable of effecting cell-specific expression wherein said promoter is operably linked to a heterologous gene, and wherein said cassette resides between said inverted terminal repeats.

2. The vector of claim 1 wherein each of said inverted terminal repeats comprises the nucleotides of SEQ ID NO:1.

3. The vector of claim 1 wherein each of said inverted terminal repeats comprises nucleotides 1 to 125 of SEQ ID NO:1.

4. The vector of claim 1 wherein said heterologous gene encodes a biologically functional protein.

5. The vector of claim 1 wherein said heterologous gene encodes a non-biologically functional protein.

6. The vector of claim 1 wherein said heterologous gene encodes an antisense RNA.

7. The vector of claim 1 wherein said heterologous gene is selected from the group consisting of a gene encoding α-globin, β-globin, γ-globin, granulocyte macrophage-colony stimulating factor (GM-CSF), tumor necrosis factor (TNF), any one of interleukins 1–11, neomycin resistance, luciferase, adenine phosphoribosyl transferase (APRT), retinoblastoma, insulin, mast cell growth factor, p53, adenosine deaminase.

8. The vector of claim 1 wherein said heterologous gene encodes P-glycoprotein.

9. The vector of claim 6 wherein said antisense RNA is complementary to a segment of the DNA or RNA encoding α-globin.

10. The vector of claim 1 wherein said vector is AAV-B19-mdr.

11. A host cell transfected by the vector of any one of claims 1–10.

12. The host cell of claim 11 wherein said cell is a hematopoietic stem or hematopoietic progenitor cell.

13. A virion comprising the vector of any one of claims 1–9.

14. A host cell infected by the virion of claim 13.

15. The host cell of claim 14 wherein said cell is a hematopoietic stem or progenitor cell.

* * * * *